United States Patent
Wataya et al.

(10) Patent No.: US 12,408,829 B2
(45) Date of Patent: Sep. 9, 2025

(54) IMAGE PICKUP UNIT AND ENDOSCOPE APPLYING THE SAME

(71) Applicant: OLYMPUS MEDICAL SYSTEMS CORP., Tokyo (JP)

(72) Inventors: Yuichi Wataya, Akiruno (JP); Tetsuta Hanawa, Hachioji (JP); Sho Saito, Akishima (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 122 days.

(21) Appl. No.: 18/389,329

(22) Filed: Nov. 14, 2023

(65) Prior Publication Data
US 2024/0074645 A1    Mar. 7, 2024

Related U.S. Application Data

(63) Continuation of application No. PCT/JP2021/029715, filed on Aug. 12, 2021.

(51) Int. Cl.
*A61B 1/05* (2006.01)
*A61B 1/00* (2006.01)
(Continued)

(52) U.S. Cl.
CPC ............ *A61B 1/05* (2013.01); *A61B 1/00018* (2013.01); *A61B 1/0011* (2013.01); *H04N 23/55* (2023.01); *H04N 23/555* (2023.01); *H04N 25/79* (2023.01)

(58) Field of Classification Search
CPC ..... A61B 1/05; A61B 1/00018; A61B 1/0011; A61B 1/051; A61B 1/04; H04N 23/55;
(Continued)

(56) References Cited

U.S. PATENT DOCUMENTS

| 9,118,825 B2* | 8/2015 | Singh | .................... H10F 39/804 |
| 2011/0037886 A1* | 2/2011 | Singh | .................... H10F 39/804 |
| | | | 348/340 |

(Continued)

FOREIGN PATENT DOCUMENTS

| JP | H05-211997 A | 8/1993 |
| JP | 2001-212074 A | 8/2001 |

(Continued)

OTHER PUBLICATIONS

International Search Report dated Oct. 19, 2021 received in PCT/JP2021/029715.

*Primary Examiner* — Albert H Cutler
(74) *Attorney, Agent, or Firm* — Scully, Scott, Murphy & Presser, P.C.

(57) ABSTRACT

An image pickup unit includes: an image pickup optical system including an optical axis; an image pickup device; a first electric substrate on which the image pickup device is mounted; a second electric substrate formed integrally with the first electric substrate and configured to surround peripheries of the image pickup optical system and the image pickup device and extend in a direction along the optical axis, the second electric substrate including a housing space for housing the image pickup optical system and the image pickup device, a part of the second electric substrate being formed in an arc shape when viewed in a cross section in a vertical direction with respect to the optical axis; and a conductive circuit connecting the first and second electric substrates, and provided from a first surface exposed outside of the second electric substrate to a second surface in the housing space.

20 Claims, 18 Drawing Sheets

(51) Int. Cl.
*H04N 23/50* (2023.01)
*H04N 23/55* (2023.01)
*H04N 25/79* (2023.01)

(58) Field of Classification Search
CPC ...... H04N 23/555; H04N 25/79; H04N 23/50;
H04N 23/51; H04N 23/54; H04N 23/57;
H04N 23/00; H04N 23/60; G03B 30/00;
G02B 13/001
See application file for complete search history.

(56) References Cited

U.S. PATENT DOCUMENTS

| | | | | | |
|---|---|---|---|---|---|
| 2012/0140101 | A1* | 6/2012 | Afshari | ................ | H04N 23/57 |
| | | | | | 348/335 |
| 2014/0092296 | A1* | 4/2014 | Han | ................ | H05K 1/181 |
| | | | | | 348/373 |
| 2015/0319378 | A1* | 11/2015 | Hoelter | ................ | H04N 23/51 |
| | | | | | 348/164 |
| 2017/0127915 | A1* | 5/2017 | Viebach | ................ | A61B 1/018 |
| 2018/0277583 | A1* | 9/2018 | Harazono | ........... | H10F 39/8057 |
| 2021/0044731 | A1* | 2/2021 | Song | ................ | G02B 7/02 |
| 2023/0043603 | A1* | 2/2023 | Hirao | ................ | G02B 7/021 |

FOREIGN PATENT DOCUMENTS

| | | | |
|---|---|---|---|
| JP | 2006-237276 | A | 9/2006 |
| JP | 2008-272298 | A | 11/2008 |
| JP | 2009-039434 | A | 2/2009 |
| JP | 5958727 | B2 | 8/2016 |
| JP | 2018-165786 | A | 10/2018 |
| JP | 6533787 | B2 | 6/2019 |
| JP | 2019-195382 | A | 11/2019 |
| JP | 2020-010825 | A | 1/2020 |

* cited by examiner

IMAGE PICKUP UNIT AND ENDOSCOPE APPLYING THE SAME

CROSS REFERENCE TO RELATED APPLICATION

This application is a continuation application of PCT/JP2021/029715 filed on Aug. 12, 2021, the entire contents of which are incorporated herein by this reference.

BACKGROUND OF THE INVENTION

1. Field of the Invention

The present invention relates to an image pickup unit and an endoscope applying the image pickup unit, the image pickup unit being provided in a distal end portion of an insertion portion of the endoscope and configured to pick up an image inside a subject.

2. Description of the Related Art

Conventionally, endoscopes configured by including an insertion portion formed in an elongated tube shape have been widely used in medical fields and industrial fields, for example. Among these endoscopes, medical endoscopes for use in the medical fields have a function of acquiring images of a lesion part and the like inside an organ, etc., in a living body by an insertion portion provided with an image pickup unit being inserted into a body cavity of the living body, for example. Then, a user performs observation or examination of a state of the lesion part and the like, based on the acquired images. Industrial endoscopes for use in the industrial fields have a function of acquiring images of a flaw, corrosion, and the like in an apparatus or a machine facility, such as a jet engine, a factory pipeline, or the like, by an insertion portion provided with an image pickup unit being inserted into the apparatus or the machine facility, for example. Then, a user performs observation or examination of states of the flaw, the corrosion, and the like, based on the acquired images.

In a conventional image pickup unit applied to an endoscope, as means for achieving miniaturization of the image pickup unit while maintaining functions thereof, various kinds of ingenuities are proposed. For example, Japanese Patent Application Laid-Open Publication Nos. 2006-237276 and 2020-10825 propose ingenuities for expanding an area for mounting electronic components on an electric circuit substrate (hereinafter, shortly referred to as an electric substrate), or for achieving high density mounting of the components.

As alternative technical means for miniaturizing a conventional image pickup unit, for example, Japanese Patent Application Laid-Open Publication No. 2018-165786 and Japanese Patent No. 5958727 propose various kinds of configurations for integrally forming an image pickup device and an image pickup optical system.

Furthermore, in recent years, as technical means for achieving miniaturization of an image pickup unit, a technique for forming a solid electric substrate by using an MID (Molded Interconnect Device) has been generally put into a practical use. The MID is a three-dimensional molded interconnect device in which a wiring for electric circuit is integrally formed on a surface of a solid molded article such as an injection molded article. Unlike a conventional two-dimensional circuit (planar circuit), such an MID technique is used to enable a wiring for electric circuit to be formed on an inclined surface, a vertical surface, a curved surface, or in a through hole formed in a molded body, etc.

SUMMARY OF THE INVENTION

An image pickup unit according to one aspect of the present invention includes: an image pickup optical system including an optical axis; an image pickup device configured to pick up an optical image formed by the image pickup optical system; a first electric substrate on which the image pickup device is mounted; a second electric substrate configured of a component formed integrally with the first electric substrate, the second electric substrate being configured to surround peripheries of the image pickup optical system and the image pickup device and extend in a direction along the optical axis, the second electric substrate including a housing space for housing the image pickup optical system and the image pickup device, an inside of the housing space having a quadrangular prism shape, at least a part of the second electric substrate being formed in an arc shape when viewed in a cross section in a vertical direction with respect to the optical axis; and a conductive circuit configured to connect the first electric substrate and the second electric substrate, the conductive circuit being provided continuously from a first surface to a second surface of the second electric substrate, the first surface being exposed outside, the second surface facing the periphery of the image pickup optical system in the housing space.

An endoscope according to one aspect of the present invention includes: an image pickup unit that includes: an image pickup optical system including an optical axis; an image pickup device configured to pick up an optical image formed by the image pickup optical system; a first electric substrate on which the image pickup device is mounted; a second electric substrate configured of a component formed integrally with the first electric substrate, the second electric substrate being configured to surround peripheries of the image pickup optical system and the image pickup device and extend in a direction along the optical axis, the second electric substrate including a housing space for housing the image pickup optical system and the image pickup device, an inside of the housing space having a quadrangular prism shape, at least a part of the second electric substrate being formed in an arc shape when viewed in a cross section in a vertical direction with respect to the optical axis; and a conductive circuit configured to connect the first electric substrate and the second electric substrate, the conductive circuit being provided continuously from a first surface to a second surface of the second electric substrate, the first surface being exposed outside, the second surface facing the periphery of the image pickup optical system in the housing space. The endoscope further includes an insertion portion configured to be inserted into a subject in a predetermined insertion direction, and an image pickup unit holding portion provided at a distal end of the insertion portion and configured to hold the image pickup unit.

DETAILED DESCRIPTION OF THE PREFERRED EMBODIMENT(S)

Figure 1:
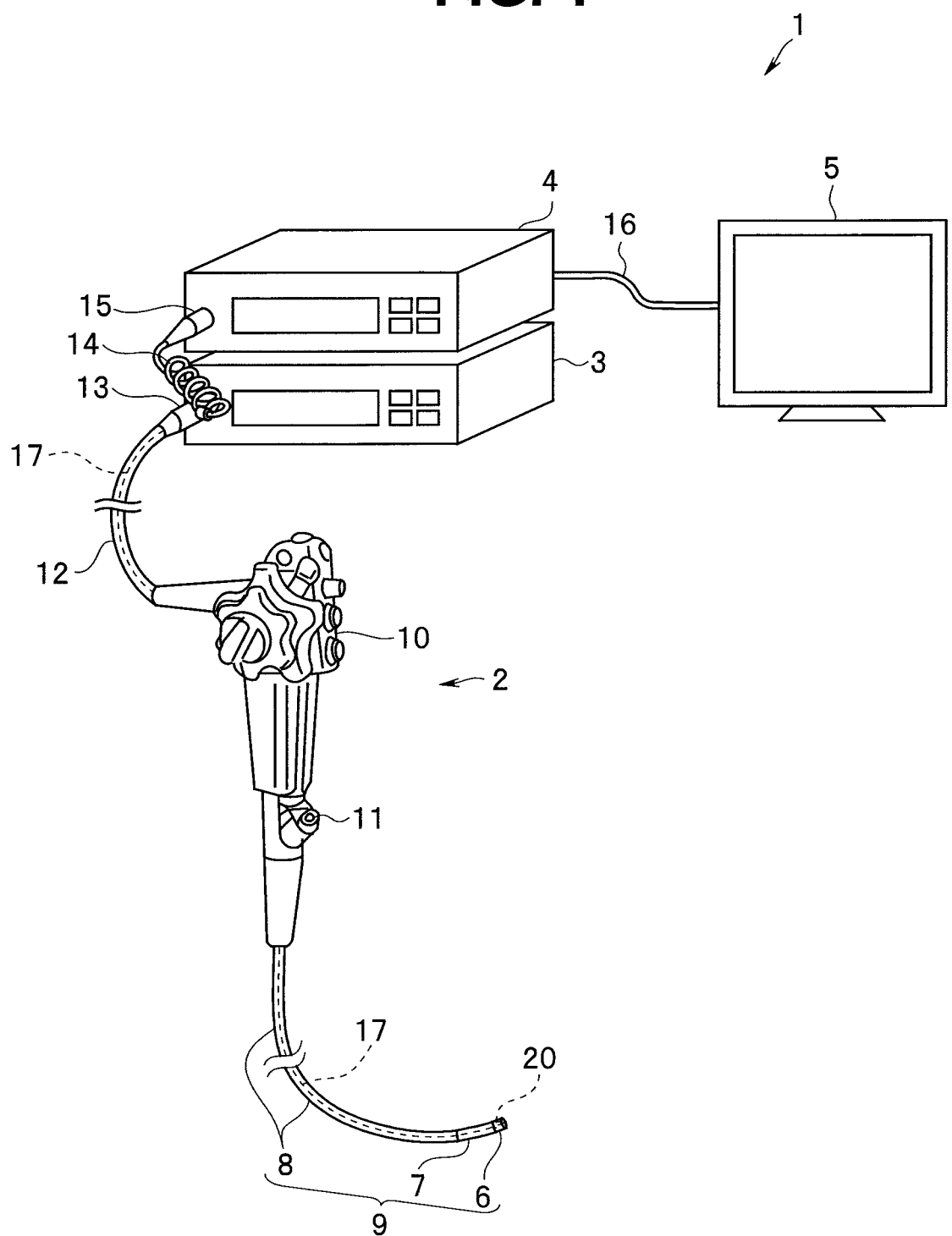
FIG. 1 is an exterior view showing an endoscope system including an endoscope to which an image pickup unit of an embodiment of the present invention is applied.

Generally, the number of components in endoscopes and image pickup units and the like applied to the endoscopes has tended to increase with a multi-functionality and an improved performance in recent years. With the increase in the number of components used, the number of processes for assembling adjustment and the like tend to increase in manufacturing conventional endoscopes or conventional image pickup units. Therefore, assembly time for endoscopes, image pickup units, and the like has tended to become longer in recent years. As a result, in recent years, there has arisen a problem of an increase in manufacturing costs of endoscopes, image pickup units, and the like.

In addition, there is constantly a strong demand for miniaturization of conventional endoscopes and image pickup units, and an ingenuity has been constantly made for responding to such a demand. However, in order to manufacture compact, multi-functional, and high-performance endoscopes and image pickup units, higher machining accuracy is desired, which leads to a tendency that difficulty in the assembling process at the time of manufacturing increases year by year.

For example, image pickup units applied to endoscopes have a noticeable tendency that pixel spacing is reduced with a high-pixelation of image pickup devices. If an image pickup device has refined pixel spacing, there is a concern for a degradation of an image quality of an image to be acquired. In order to suppress such a degradation of the image quality, it is necessary to improve processing accuracy and assembling accuracy of an image pickup optical system included in an image pickup unit, for example.

In addition, for example, an image pickup optical system to be applied to an image pickup unit includes a plurality of optical lenses, and the plurality of optical lenses have to be adjusted such that optical axes thereof are coincident with one another. Furthermore, in order to surely maintain the state where the optical axes of the respective optical lenses are coincident with one another, the plurality of optical lenses are held by using a holding member such as a lens barrel or the like. As a result, it takes a lot of time for assembling adjustment in assembling the image pickup optical system.

Furthermore, some image pickup units to be used in an oblique-view endoscope or a side-view endoscope, for example, have a configuration in which an image pickup optical system includes a prism and the like. In the oblique-view endoscope applying the image pickup unit having such a configuration, high processing accuracy is required for a prism and the like.

For example, in the image pickup unit disclosed in Japanese Patent Application Laid-Open Publication No. 2006-237276, a solid electric substrate is configured by connecting a plurality of independent electric substrates.

However, the configuration of the conventional image pickup unit disclosed in the Japanese Patent Application Laid-Open Publication No. 2006-237276 has such a problem that the number of components increases and assembling adjustment of each of electric substrates is required.

In addition, in the image pickup unit disclosed in Japanese Patent Application Laid-Open Publication No. 2020-10825, for example, a solid electric substrate is configured by bending a flexible printed circuit board.

However, since the flexible printed circuit board is applied in the configuration of the conventional image pickup unit disclosed in the Japanese Patent Application Laid-Open Publication No. 2020-10825, a holding component for holding the board is additionally required, which causes such a problem that the number of components increases.

For example, the image pickup unit disclosed in Japanese Patent Application Laid-Open Publication No. 2018-165786 includes a spacer member between an image pickup optical system and an image pickup device, to configure the image pickup optical system and the image pickup device integrally. The spacer member includes a plurality of contact surfaces each having a height variable in an optical axis direction. In addition, the image pickup optical system includes contact portions configured to contact the respective contact surfaces of the spacer member. Such a configuration enables an interval between the image pickup optical system and the image pickup device to be adjusted easily in the image pickup unit disclosed in the publication.

However, although the configuration of the image pickup unit disclosed in the above-described Japanese Patent Application Laid-Open Publication No. 2018-165786 enables easy adjustment of the interval between the image pickup optical system and the image pickup device in the optical axis direction, the configuration has such a problem that the number of components increases.

In addition, for example, the image pickup unit disclosed in the Japanese Patent No. 5958727 is configured such that the image pickup optical system, the image pickup device, and a cover glass are bonded by adhering, and then at least a part of outer circumferential sides of the image pickup optical system, a lens barrel, the image pickup device, and a transmission cable are covered with a molding resin, to thereby enable these components to be integrated.

However, the configuration of the image pickup unit disclosed in the Japanese Patent No. 5958727 has such a problem that the manufacturing cost increases, since the configuration requires an adjustment to make the optical axis of the image pickup optical system coincident with a center position of the image pickup device and also an adjustment to dispose the image pickup surface of the image pickup device at the position accurately orthogonal to the optical axis of the image pickup optical system, when bonding the image pickup optical system, the image pickup device, and the cover glass by adhering.

On the other hand, an MID applied, as a solid electric substrate, to a conventional image pickup unit, is generally formed in a cubic body, the cross-sectional shape of which is rectangular. In a case where the cross-sectional shape of the solid electric substrate is rectangular, some problems listed below are likely to arise.

For example, there is a possibility that an excellent workability cannot be ensured in a repairing adhesion work to be performed on a part around the distal end part of the image pickup unit, when incorporating the image pickup unit into a distal end member of an insertion portion of an endoscope.

In addition, for example, when performing position adjustment of the image pickup unit, adjustment in a rotation direction with respect to the optical axis cannot be performed sufficiently, which is likely to affect an observation display image, for example, variation might occur in an appearance position of a treatment instrument and the like in an observation image during a use of the endoscope.

Furthermore, during the use of the endoscope, if a distal end part of the image pickup unit having at a distal end thereof an edge part contacts an inner surface of a subject, for example, the edge part is likely to be caught on an inner surface of a living body.

Generally, in a solid electric substrate, in a case where wirings are close to each other at a part where a wiring on a front surface side and a wiring on a rear surface side overlap with each other, for example, radio wave interference tend to occur between transmission signals transmitted through the respective wirings, which decreases a transmission quality. As a measure for avoiding such a radio wave interference by the transmission signals, it can be considered to ensure a separation distance between the respective wirings at the part where the wiring on the front surface side and the wiring on the rear surface side overlap with each other, by increasing the thickness of the substrate in the solid electric substrate.

However, if the thickness of the substrate is increased in the solid electric substrate whose cross-sectional shape is rectangular, the external shape size of the substrate increases, which causes a problem that miniaturization of the image pickup unit cannot be achieved. Furthermore, the increase in the external shape size of the image pickup unit will cause another problem that a length of the transmission path increases. Since a transmission path of an endoscope tends to be long, there is a constant demand for making the transmission path of the endoscope as short as possible in order to ensure an excellent transmission quality.

Embodiments of the present invention can provide an image pickup unit configured to be capable of reducing the number of components in the entire unit while maintaining conventional functions, or while achieving a higher performance and a larger number of functions than the conventional units, to thereby contribute to a reduction of assembling time in manufacturing as well as to a reduction in manufacturing cost, and also can provide an endoscope applying the image pickup unit.

The present invention will be hereinafter described by embodiments illustrated in drawings.

Each of the drawings used in the following description is schematic, and in order to show each constituent elements in a size that enables the constituent elements to be recognized in the drawings, there is a case where respective members may be shown so that the dimensional relationship, scales, etc., of the respective members are made different among respective constituent elements. Therefore, the present invention is not limited only to the illustrated forms with regard to the number, the shapes, the ratio of the sizes of the respective constituent elements, and the relative positional relationship of the respective constituent elements, etc., described in the respective drawings.

Before making a description on a detailed configuration of the image pickup unit of each of embodiments in the present invention, hereinafter brief description will be made first on an entire endoscope system including the endoscope to which the image pickup unit is applied, with reference to FIG. 1.

FIG. 1 is an exterior view showing the endoscope system including the endoscope to which the image pickup unit of each of embodiments of the present invention is applied. The basic configuration of the endoscope system is substantially the same as that of a conventional endoscope system. Therefore, the description below is limited only to a schematic description of respective constituent members in the endoscope system.

As shown in FIG. 1, an endoscope system 1 including an endoscope 2 to which an image pickup unit (to be detailed later; to which a reference sign 20 is added in FIG. 1) of each of the embodiments of the present invention is applied, is mainly configured of the endoscope 2, a light source apparatus 3, a video processor 4, a display apparatus 5, etc.

The endoscope 2 is configured mainly of an insertion portion 9, an operation portion 10, a universal cord 12, and the like. The insertion portion 9 has a substantially elongated tube shape. The operation portion 10 from which the insertion portion 9 is extended has a substantially box shape.

The insertion portion 9 of the endoscope 2 includes, in the following order from the distal end side, a distal end portion 6, a bending portion 7, and a flexible tube portion 8. The proximal end of the insertion portion 9 is connected to the operation portion 10.

The distal end portion 6 includes, inside thereof, the image pickup unit (reference sign 20) of the present embodiment. Detailed configuration of the image pickup unit will be described later. Note that the image pickup unit is shown with the reference sign 20 in FIG. 1. The image pickup unit 20 corresponds to the image pickup unit of the first embodiment (see FIGS. 2 to 4) of the present invention.

Image pickup units (20A, 20B, 20C, 20D, and 20E) of other embodiments of the present invention can be similarly applied to the endoscope 2.

The operation portion 10 is configured mainly of a forceps port 11, an operation portion main body, a plurality of operation members, etc. The forceps port 11 has an opening through which a treatment instrument or the like is inserted. The operation portion main body configures a grasping portion. The plurality of operation members are provided on the outer surface of the operation portion main body and used for performing various kinds of operation of the endoscope 2.

The forceps port 11 provided on the operation portion 10 configures a proximal end side opening portion of a treatment instrument channel (not shown) inserted and arranged from the operation portion 10 to a distal end side opening portion of the distal end portion 6 of the insertion portion 9.

The universal cord 12 is a tubular member extended from a lateral side of the operation portion 10. The universal cord 12 includes, at the distal end part thereof, a scope connector 13. The scope connector 13 is connected to the light source apparatus 3.

The light source apparatus 3 is an apparatus configured to supply illumination light to an illumination optical member (not shown) provided in the distal end portion 6 of the insertion portion 9 of the endoscope 2. The illumination light emitted from the light source apparatus 3 is transmitted to the distal end portion 6 of the insertion portion 9 of the endoscope 2, via an optical fiber cable 17 arranged by being inserted through the scope connector 13, the universal cord 12, the operation portion 10, and the insertion portion 9. Then, the illumination light passes through the illumination optical member (not shown) provided on the front surface of the distal end portion 6, to be applied toward an observation object (lesion part and the like) in front of the distal end portion 6.

A scope cable 14 is extended from the scope connector 13 toward the lateral side. The scope cable 14 includes, at the distal end part thereof, an electrical connector portion 15. The electrical connector portion 15 is connected to the video processor 4.

The video processor 4 is a control apparatus configured to control the entirety of the endoscope system 1. In this case, the video processor 4 includes a signal processing circuit, a control processing circuit, and the like. The signal processing circuit is configured to receive an image pickup signal from the image pickup unit 20 provided in the distal end portion 6 of the insertion portion 9 of the endoscope 2, to perform predetermined signal processing. The control processing circuit is configured to output a control signal for driving the image pickup unit 20 and the like.

For such signal transmission, a signal transmission cable (not shown) is disposed from the video processor 4 to an internal configuration unit (for example, the image pickup unit 20, etc.) of the distal end portion 6. The signal transmission cable is arranged by being inserted through the electrical connector portion 15, the scope cable 14, the scope connector 13, the universal cord 12, the operation portion 10, and the insertion portion 9, for example.

With such a configuration, for example, the image pickup signal outputted from the image pickup unit 20, the control signal outputted from the video processor 4, and other signals are transmitted between the image pickup unit 20 and the video processor 4 through the signal transmission cable. One form of the signal transmission cable includes, for example, a composite cable configured by bundling a plurality of cables and covering the cables with an outer cover shield, an outer cover tube, or the like.

The video processor 4 and the display apparatus 5 are connected to each other by using a video cable 16. The video cable 16 is configured to transmit an image signal, the control signal, and the like outputted from the video processor 4 to the display apparatus 5.

The display apparatus 5 is configured to receive the image signal, the control signal, and the like outputted from the video processor 4, to display an endoscope image of a predetermined form and various kinds of information, in a display form according to the received control signal.

The endoscope system 1 including the endoscope 2 to which the image pickup unit 20 of each of the embodiments of the present invention is applied is configured as roughly described above. Note that other configurations in the endoscope system 1 are substantially the same as those in a conventional endoscope system of the same type.

Figure 2:
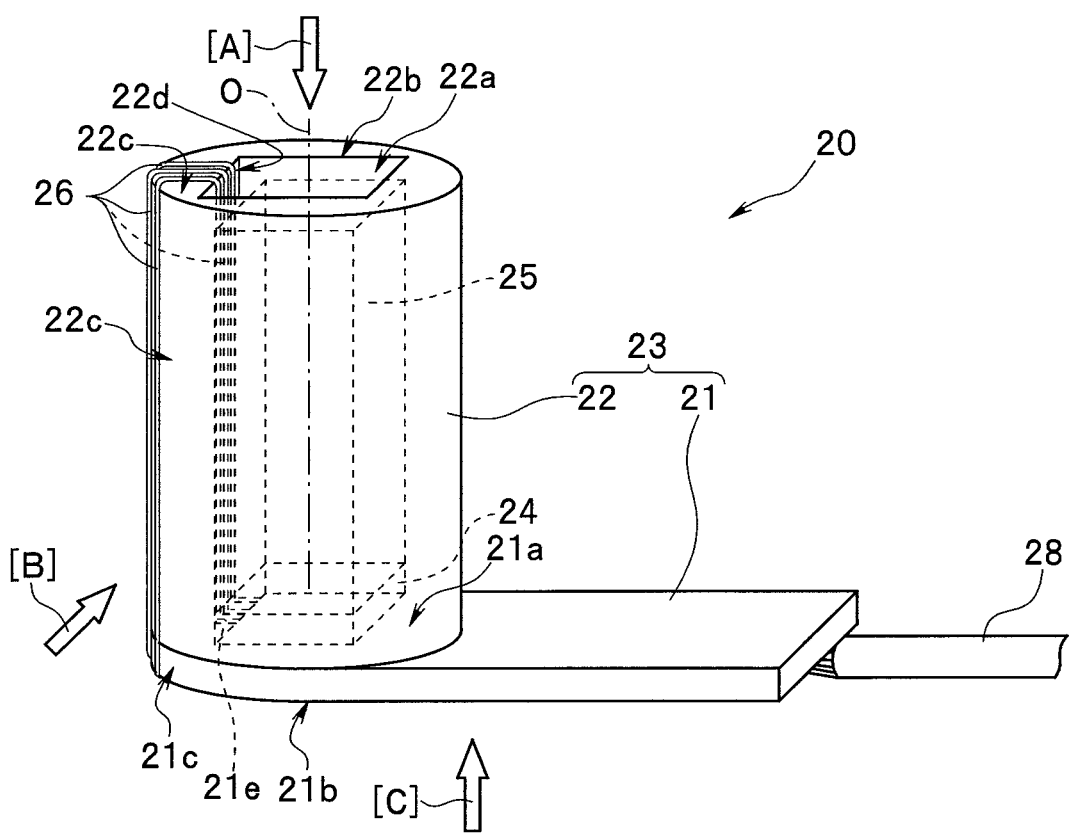
FIG. 2 is a perspective view conceptually showing an exterior of the image pickup unit of a first embodiment of the present invention.
Figure 3:
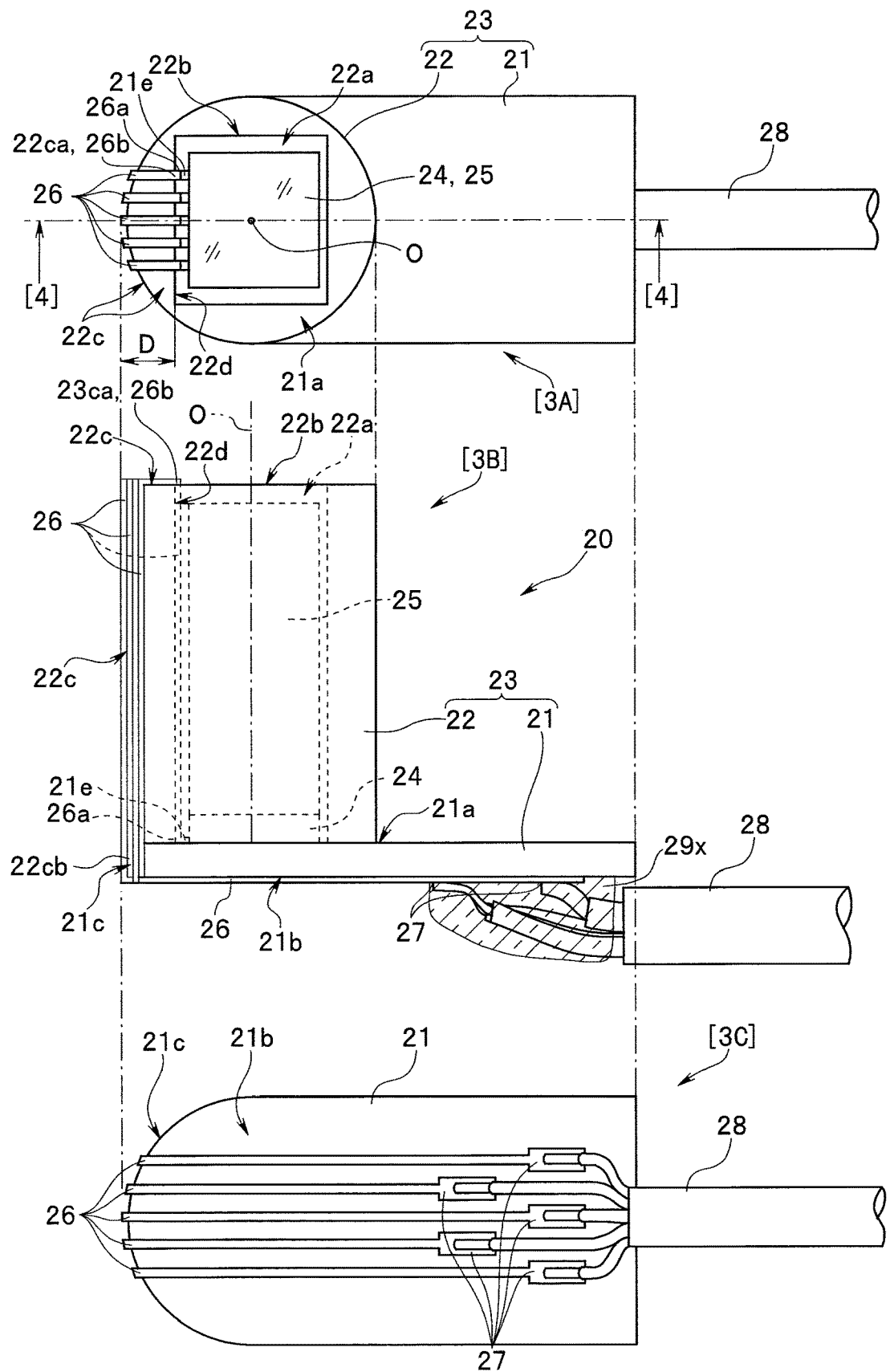
FIG. 3 is a trihedral view of the image pickup unit in FIG. 2.
Figure 4:
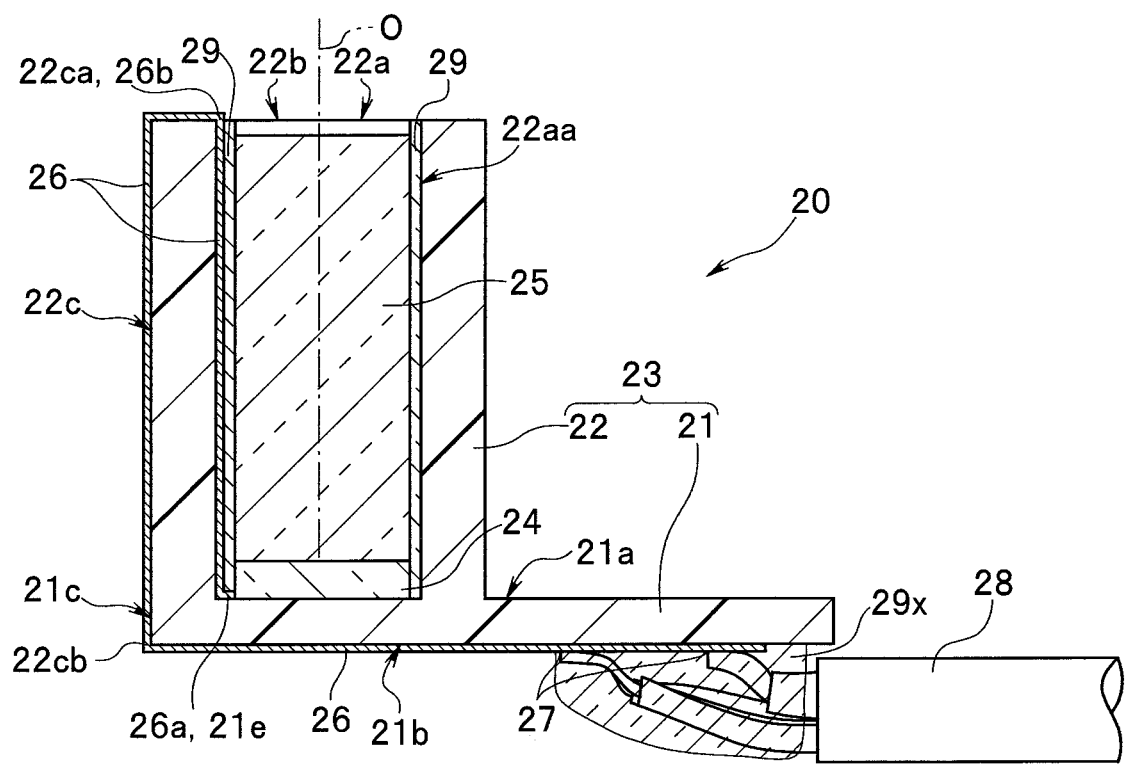
FIG. 4 is a cross-sectional view taken along the line [4]-[4] in FIG. 3.

Next, detailed description will be made on the image pickup unit of the first embodiment of the present invention with reference to FIGS. 2 to 4. FIG. 2 is a perspective view conceptually showing the exterior of the image pickup unit of the first embodiment of the present invention. FIG. 3 is a trihedral view of the image pickup unit of the present embodiment. Note that the reference sign [3A] in FIG. 3 shows a top view which is viewed in the direction of the arrow [A] in FIG. 2. In addition, the reference sign [3B] in FIG. 3 shows a side view which is viewed in the direction of the arrow [B] in FIG. 2. The reference sign [3C] in FIG. 3 shows a bottom view which is viewed in the direction of the arrow [C] in FIG. 2. FIG. 4 is a cross-sectional view taken along the line [4]-[4] in FIG. 3.

As shown in FIGS. 2 to 4, the image pickup unit 20 of the present embodiment includes a solid electric substrate 23 constituted of a first electric substrate 21 and a second electric substrate 22, an image pickup device 24, an image pickup optical system 25, and a conductive circuit 26.

The image pickup optical system 25 is an optical unit constituted of a plurality of optical lenses that form an optical image of an observation object (lesion part or the like) in a subject. The plurality of optical lenses constituting the image pickup optical system 25 are held, with optical axes O of the respective lenses being made coincident with one another. Note that, in FIGS. 2 to 4, the image pickup optical system 25 is shown as one member, by omitting the detailed illustration of the plurality of optical lenses and the like. In this case, the image pickup optical system 25 shown in FIGS. 2 to 4 is formed in a substantially quadrangular prism shape as a whole, as an example. The reason why the image pickup optical system 25 has the substantially quadrangular prism shape in the configuration example is that the shape of the image pickup optical system 25 is formed in accordance with the rectangular shape of the image pickup surface of the image pickup device 24. Therefore, the shape of the image pickup optical system 25 is not limited to that in the configuration example and may be a different shape.

The image pickup device 24 is an electronic component configured by including a photoelectric conversion device, an electric circuit, and the like. The photoelectric conversion device is configured to receive an optical image formed by the image pickup optical system 25 to convert the received optical image into an electric image signal, and the electric circuit is configured to drive and control the photoelectric conversion device. The image pickup device 24 is mounted at a predetermined position on the first electric substrate 21.

The image pickup device 24 is manufactured, for example, in such a manner that a plurality of devices formed on a wafer by a wafer process are divided into individual chips (singulated) by cutting the wafer by a dicing process. Therefore, the image pickup device 24 has a cross section formed in a rectangular shape. In addition, as described above, the image pickup optical system 25 is formed in the substantially quadrangular prism shape in accordance with the cross-sectional shape of the image pickup device 24. In the image pickup unit 20 of the present embodiment, the image pickup device 24 and the image pickup optical system 25 are integrated by using a casing member 29 (see FIG. 4) such as a heat-shrinkable tube or an adhesive, for example.

The light-receiving surface (image pickup surface) of the image pickup device 24 is placed in parallel with a plane (orthogonal plane) in the vertical direction with respect to the optical axis O of the image pickup optical system 25. In addition, the optical axis O of the image pickup optical system 25 is arranged at a substantially center position of the light-receiving surface (image pickup surface) of the image pickup device 24.

The solid electric substrate 23 is an electric substrate configured three-dimensionally by integrally forming the first electric substrate 21 and the second electric substrate 22. In the image pickup unit 20 of the present embodiment, the solid electric substrate 23 is formed by the MID (Molded Interconnect Device), for example. Note that the solid electric substrate 23 is not limited to the molded component configured by the MID, but may be configured such that, after each of the first electric substrate 21 and the second electric substrate 22 is formed, the first and second electric substrates are integrally connected, and then the conductive circuit is provided at a predetermined position on a surface of the integrally connected substrate, for example.

The first electric substrate 21 is an electric substrate formed in a substantially plate shape. The image pickup device 24 is mounted at a predetermined position on a predetermined surface (see the reference sign 21*a* in FIG. 2) of the first electric substrate 21. Here, the predetermined surface (reference sign 21*a*) of the first electric substrate 21 is a surface on which the image pickup device 24 is mounted. Hereinafter, in the first electric substrate 21, the surface on which the image pickup device 24 is mounted is referred to as an image pickup device mounting surface 21*a*.

In addition, in a predetermined region on the outer surface of the first electric substrate 21, a part of the conductive circuit 26 that connects the first electric substrate 21 and the second electric substrate 22 is disposed.

In the present embodiment, as an example, the conductive circuit 26 is formed such that a part thereof is formed on a bottom surface 21*b* of the first electric substrate 21, and another part thereof is formed on a side surface 21*c* of the first electric substrate 21, as shown in the drawing. In this case, the part of the conductive circuit 26 formed on the bottom surface 21*b* is continuous with the other part of the conductive circuit 26 formed on the side surface 21*c*, and the other part of the conductive circuit 26 formed on the side surface 21*c* is continuous with yet another part of the conductive circuit 26 formed on a first surface 22*c* of the second electric substrate 22 to be described later.

A cable connecting land 27 is provided in a tip region of the part of the conductive circuit 26 formed on the bottom surface 21*b* of the first electric substrate 21. The cable connecting land 27 is a soldering region provided on the first electric substrate 21, for connecting the signal transmission cable 28 and the conductive circuit 26.

Note that the signal transmission cable 28 is a cable wire for signal transmission extended from an external device (video processor 4, for example). The signal transmission cable 28 is soldered to the cable connecting land 27, to thereby allow the external device and the image pickup device 24 to be electrically connected to each other through the signal transmission cable 28, the cable connecting land 27, and the conductive circuit 26. Such a configuration enables an electric signal to be transmitted and received between the external device and the image pickup device 24. Note that an outer surface of a connecting part at which the signal transmission cable 28 is soldered to the cable connecting land 27 is protected with an adhesive 29*x*, or the like (see FIGS. 3 and 4).

On the other hand, the second electric substrate 22 is an electric substrate formed in a substantially cylindrical shape extending from a predetermined position on the image pickup device mounting surface 21*a* of the first electric substrate 21 in the direction along the optical axis O. Specifically, for example, the second electric substrate 22 is formed to extend from the connecting part of the first electric substrate 21 and the image pickup device 24 in the direction along the optical axis O.

The second electric substrate 22 is formed so as to include inside thereof a housing space 22*a* for housing the image pickup device 24 and the image pickup optical system 25. One end surface of the housing space 22*a* is closed by being connected to the first electric substrate 21. Therefore, the image pickup device mounting surface 21*a* of the first electric substrate 21 serves as the bottom surface of the housing space 22*a*. The image pickup device 24 is mounted at the substantially center part on the image pickup device mounting surface 21*a* serving as the bottom surface part of the housing space 22*a*.

In addition, on another end surface opposing to the bottom surface of the housing space 22*a*, a rectangular-shaped opening 22*b* is formed. Thus, the housing space 22*a* is open to the outside by the opening 22*b*. As described above, the opening 22*b* is formed in the rectangular shape. In accordance with the rectangular shape, the housing space 22*a* is formed as a substantially quadrangular prism-shaped space.

As described above, the image pickup device 24 is mounted on the bottom surface part of the housing space 22*a*, that is, the image pickup device mounting surface 21*a* of the first electric substrate 21. Furthermore, on the image pickup device 24, the image pickup optical system 25 is arranged. The image pickup device 24 and the image pickup optical system 25 are integrated by using the casing member 29 (for example, the heat-shrinkable tube or the adhesive, etc.), as described above. Thus, as described above, the outer shape of the unit configured by integrating the image pickup device 24 and the image pickup optical system 25 has a substantially quadrangular prism shape as a whole.

The unit thus configured by integrating the image pickup device 24 and the image pickup optical system 25 is housed in the housing space 22*a*. In this state, the second electric substrate 22 extends in the direction along the optical axis O, and is arranged so as to surround the side surfaces (outer circumferences or peripheries) of the image pickup device 24 and the image pickup optical system 25. The second electric substrate 22 is formed such that at least a part of thereof has an arc shape (for example, a circular shape, an elliptical shape, or the like) when viewed in a cross section in the vertical direction (orthogonal direction) with respect to the optical axis O (see the reference sign [3A] in FIG. 3).

Furthermore, the second electric substrate 22 includes, at predetermined positions on the surfaces thereof, a part of the conductive circuit 26. In more detail, the conductive circuit 26 is formed continuously from the first surface 22c to a second surface 22d of the second electric substrate 22. The first surface 22c is exposed outside and the second surface 22d serves as the inner wall surface of the housing space 22a.

In this case, as shown in FIG. 3, etc., the first surface 22c includes the outer circumferential side surface of the second electric substrate 22 and the surface of the outer peripheral edge portion of the opening 22b on the top surface side of the second electric substrate 22. In addition, as shown in FIG. 3, etc., the second surface 22d is the inner wall surface of the housing space 22a and is a surface facing the respective side surfaces of the image pickup device 24 and the image pickup optical system 25.

One end 26a (see FIG. 4, etc.) of the part of the conductive circuit 26 on the second surface 22d is connected to a connecting part 21e. At the connecting part 21e, the one end 26a is connected to the image pickup device 24 mounted on the bottom surface part of the housing space 22a. Another end 26b (see FIG. 4, etc.) of the part of the conductive circuit 26 on the second surface 22d is connected to one end 22ca of the part of the conductive circuit 26 on the first surface 22c. Another end 22cb (see FIG. 4, etc.) of the part of the conductive circuit 26 on the first surface 22c is connected to the part of the conductive circuit 26 on the side surface 21c of the first electric substrate 21.

Thus, the conductive circuit 26 is provided continuously from the connecting part 21e at which the one end 26a is connected to the image pickup device 24 to the part of the conductive circuit 26 on the first electric substrate 21, via the second surface 22d and the first surface 22c of the second electric substrate 22. Thus, the conductive circuit 26 connects the first electric substrate 21 and the second electric substrate 22, to thereby connect the image pickup device 24 and the signal transmission cable 28 through the first electric substrate 21 and the second electric substrate 22.

Note that, in the state where the image pickup device 24 and the image pickup optical system 25 are housed inside the housing space 22a, a clearance space 22aa (see FIG. 4) between the inner wall of the housing space 22a and the image pickup device 24 and image pickup optical system 25 is filled with the casing member 29 (see FIG. 4) such as the adhesive or the like.

As described above, according to the first embodiment, in the image pickup unit 20, the solid electric substrate 23 configured by the first electric substrate 21 and the second electric substrate 22 being integrally formed is employed, and the second electric substrate 22 is formed by including the housing space 22a in which the image pickup optical system 25 and the image pickup device 24 are housed, to surround the peripheries of the image pickup optical system 25 and the image pickup device 24, and extends in the direction along the optical axis O. In addition, the second electric substrate 22 is formed such that at least a part thereof has the arc shape when viewed in the cross section in the vertical direction with respect to the optical axis O.

In other words, in the present embodiment, the second electric substrate 22 is used as a substitute for a lens barrel as a holding frame for holding the image pickup optical system 25, to thereby enable the unit, which is configured by integrating the image pickup device 24 and the image pickup optical system 25, to be formed integrally with the solid electric substrate 23, with the unit housed in the housing space 22a of the solid electric substrate 23.

Such a configuration can contribute to the reduction of the number of components as well as to the reduction of assembling time, to thereby be capable of contributing to the reduction of the manufacturing cost.

In addition, the second electric substrate 22 is configured such that at least a part thereof has the arc shape when viewed in the cross section in the vertical direction with respect to the optical axis O, while enabling the substantially quadrangular prism-shaped unit configured by integrating the image pickup device 24 and the image pickup optical system 25 to be housed in the housing space 22a, to thereby be capable of obtaining the preferable effects as described below.

For example, it is possible to ensure an excellent workability in a repairing adhesion working to be performed on a part around the distal end part of the image pickup unit 20, when the image pickup unit 20 is incorporated into the distal end portion of the insertion portion of the endoscope.

In addition, when the position adjustment of the image pickup unit 20 is performed, for example, it is possible to perform the position adjustment in the rotation direction with respect to the optical axis O. Such position adjustment enables an observation display image during the use of the endoscope to be adjusted to a suitable state. For example, it is possible to perform such adjustment that a treatment instrument and the like appears at a predetermined position in the observation display image.

Furthermore, even if the distal end part of the image pickup unit 20 contacts the inner wall of the subject during the use of the endoscope, for example, the possibility that the image pickup unit 20 is caught on the inner wall of a living body can be eliminated. Thus, the smooth and safe use of the endoscope can be ensured.

In addition, the second electric substrate 22 in the solid electric substrate 23 is configured such that at least a part thereof has the arc shape (substantially circular shape) when viewed in the cross section in the vertical direction with respect to the optical axis O and the shape in the housing space 22a is the substantially quadrangular prism shape. Such a configuration can ensure a separation distance (see the reference sign D in FIG. 3) between the respective wirings (respective parts of the conductive circuit 26) disposed on the respective surfaces of the substrate, without increasing the thickness of the substrate. As a result, such a configuration enables an excellent transmission quality to be ensured.

In other words, in the second electric substrate 22, the part of the conductive circuit 26 disposed on the first surface 22c and the part of the conductive circuit 26 disposed on the second surface 22d are separated from each other by the sufficient separation distance D due to the thickness of the second electric substrate 22.

If the outer shape of the solid circuit substrate and the inner shape of the housing space are substantially the same, a wall portion with a uniform thickness is formed. In this case, in order to ensure the separation distance between the first surface (surface exposed outside) and the second surface (inner wall surface of the housing space), the thickness of the substrate needs to be set to a large thickness. However, in that case, the size of the outer shape will increase.

In contrast, in the solid electric substrate 23 of the present embodiment, the second electric substrate 22 is formed such that at least a part thereof has the arc shape (specifically, substantially the circular shape) when viewed in the cross section in the vertical direction with respect to the optical axis O, and the housing space 22a has the substantially rectangular shape when viewed in the cross section. With such a configuration, the present embodiment can ensure the sufficient separation distance D between the first surface 22c (surface exposed outside) and the second surface 22d (inner wall surface of the housing space) in the second electric substrate 22.

Note that, in the image pickup unit 20 of the above-described first embodiment, as an example, the second electric substrate 22 of the solid electric substrate 23 is formed in the substantially circular shape, when viewed in the cross section in the vertical direction with respect to the optical axis O. However, the image pickup unit of the present invention is not limited to the above-described configuration example. In other words, in the image pickup unit of the present invention, the second electric substrate in the solid electric substrate may have a different configuration as long as at least a part of the second electric circuit has an arc shape when viewed in the cross section in the vertical direction with respect to the optical axis O. The second electric substrate may have the shape as shown in FIG. 5, for example.

Figure 5:
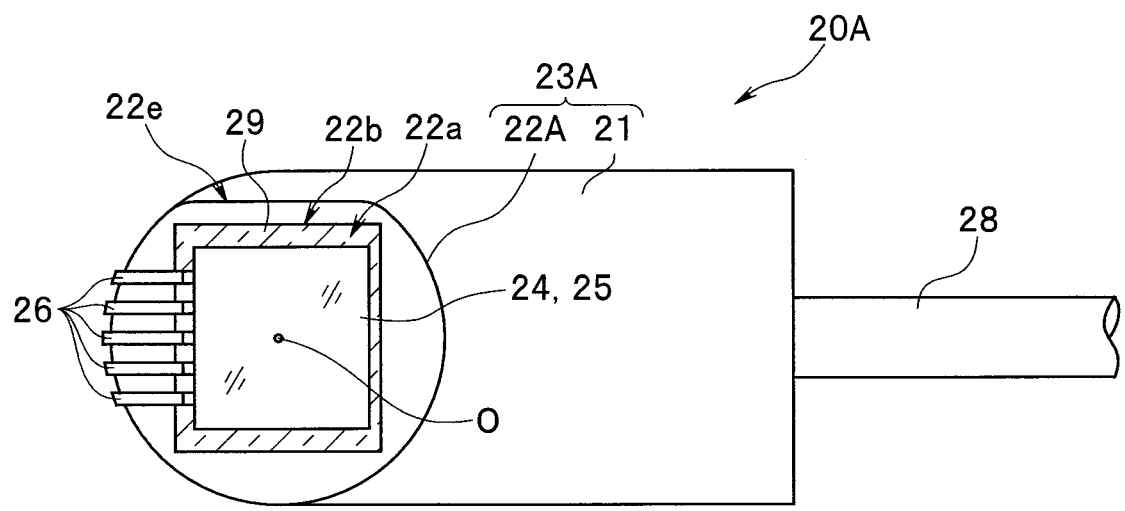
FIG. 5 shows a modification of the image pickup unit of the first embodiment of the present invention, and is a plan view of the image pickup unit of the modification when viewed from a top surface.

FIG. 5 shows a modification of the image pickup unit of the above-described first embodiment. FIG. 5 is a plan view of the image pickup unit of the modification when viewed from the top surface. As shown in FIG. 5, a solid electric substrate 23A in an image pickup unit 20A of the modification includes a second electric substrate 22A formed in a substantially circular shape as a whole, when viewed in the cross section in the vertical direction with respect to the optical axis O, and the second electric substrate 22A has a cutout portion 22e formed by a part of an outer circumference of the second electric substrate 22A being cut. Other configurations are the same as those of the above-described image pickup unit 20.

Even if the second electric substrate 22A thus configured is employed, exactly the same effects as those of the above-described first embodiment can be obtained.

Figure 6:
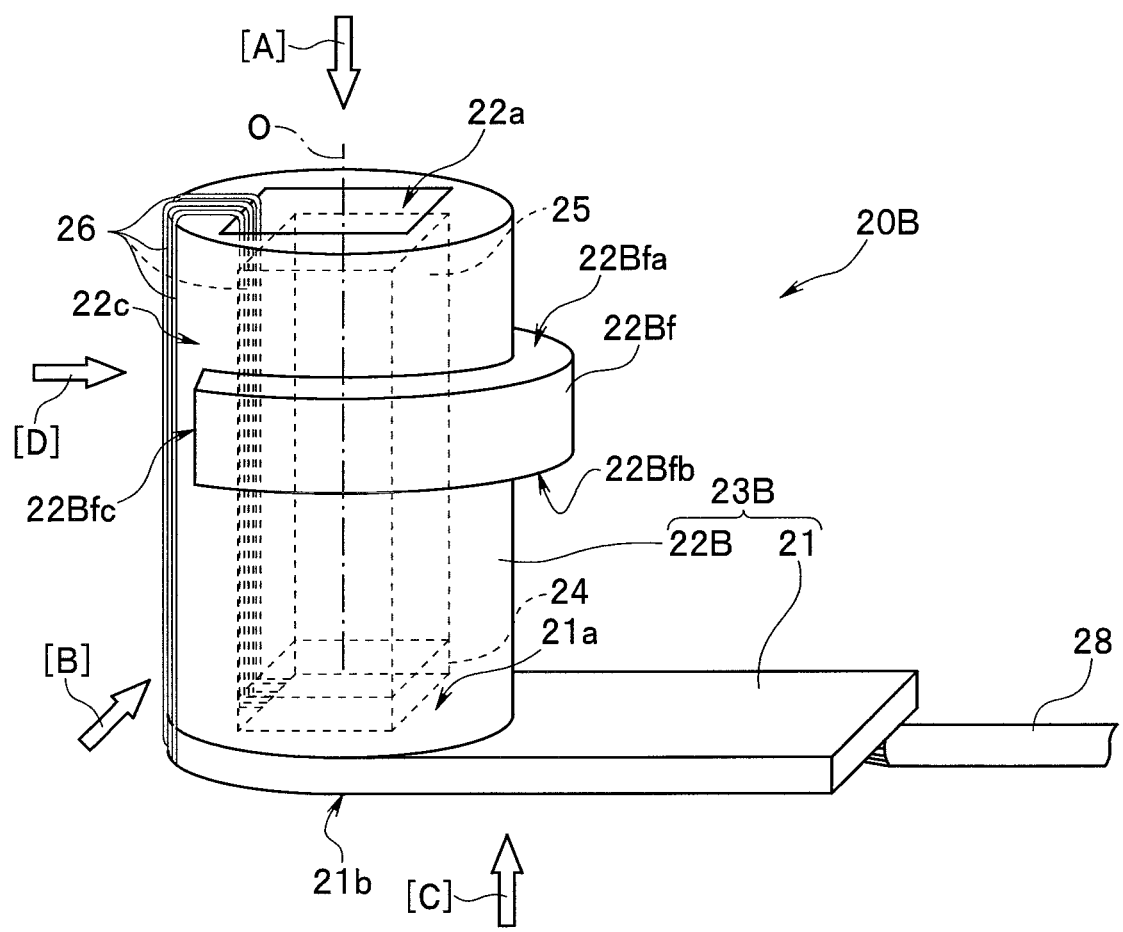
FIG. 6 is a perspective view conceptually showing an exterior of an image pickup unit of a second embodiment of the present invention.
Figure 7:
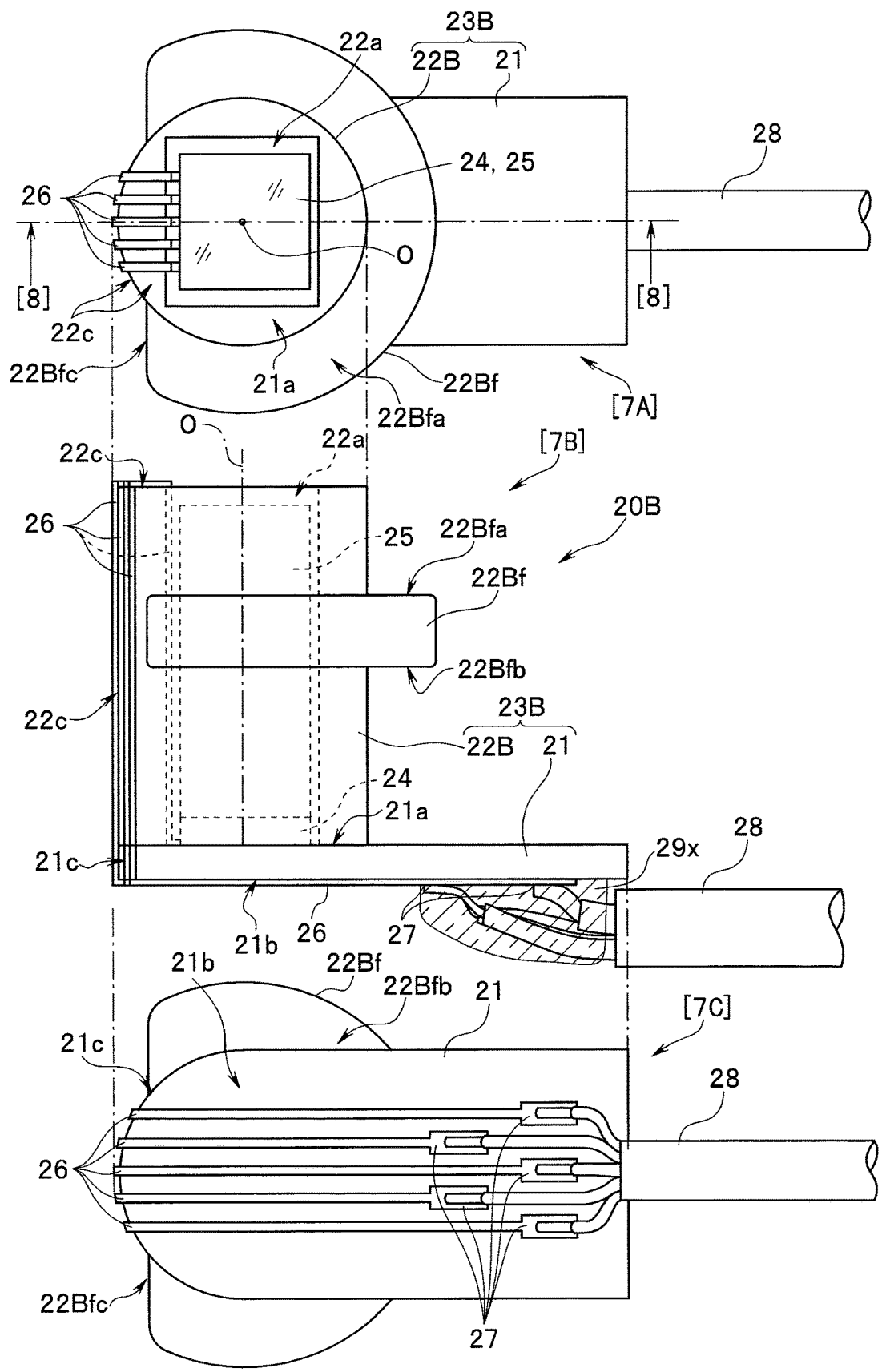
FIG. 7 is a trihedral view of the image pickup unit of the second embodiment of the present invention.
Figure 8:
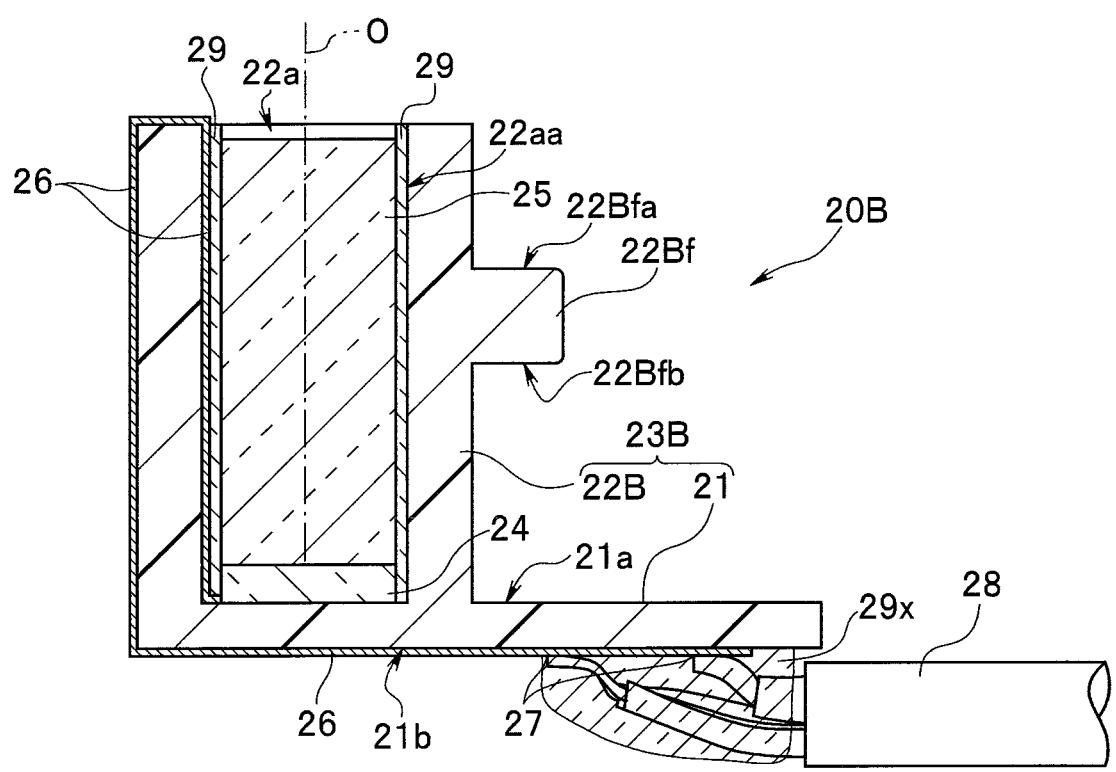
FIG. 8 is a cross-sectional view taken along the line [8]-[8] in FIG. 6.
Figure 9:
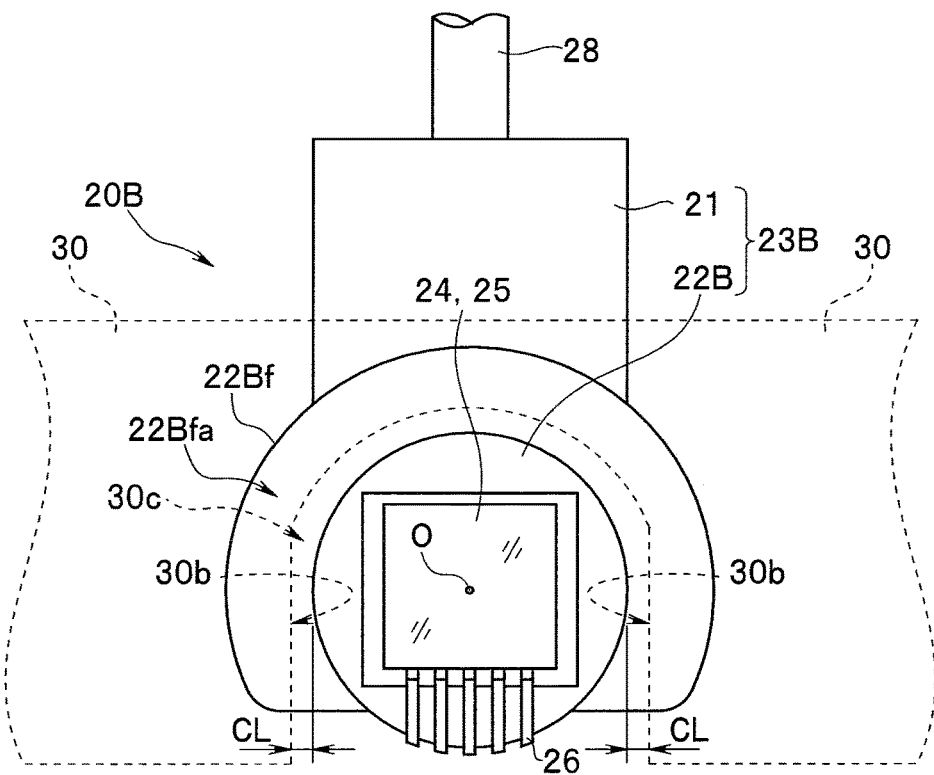
FIG. 9 is a view conceptually showing an optical axis adjusting process when incorporating the image pickup unit of the second embodiment of the present invention into a distal end portion of an insertion portion of an endoscope, and is a plan view of the image pickup unit when viewed from a top surface side.
Figure 10:
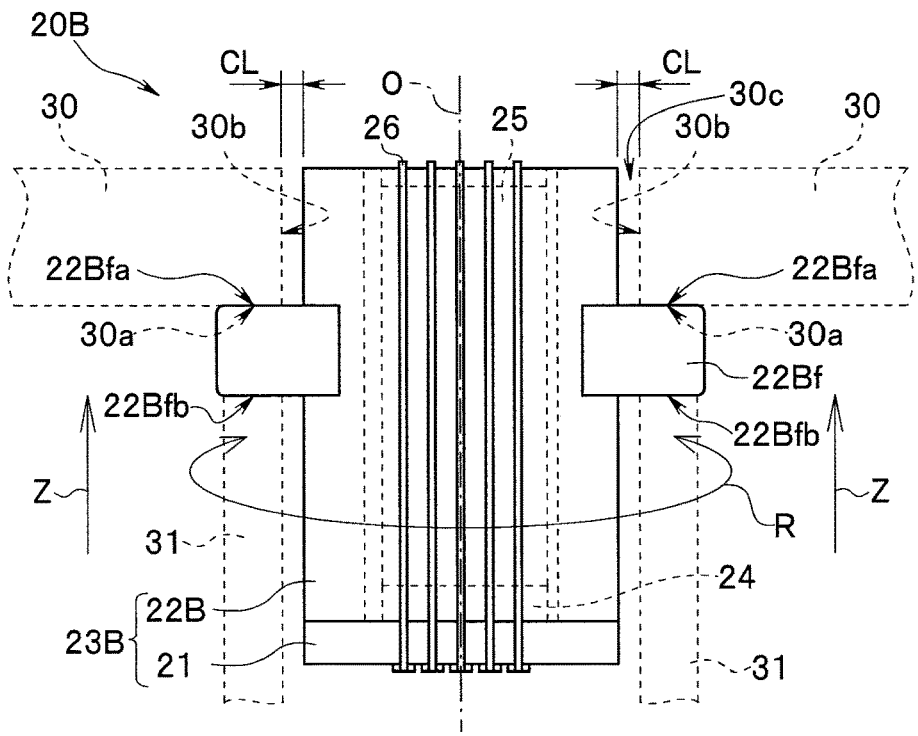
FIG. 10 is a front view of the image pickup unit in FIG. 9 when viewed in a direction corresponding to the arrow [D] in FIG. 6.

Next, description will be made below on an image pickup unit of the second embodiment of the present invention, with reference to FIGS. 6 to 10. FIG. 6 is a perspective view conceptually showing an exterior of the image pickup unit of the second embodiment of the present invention. FIG. 7 is a trihedral view of the image pickup unit of the present embodiment. Note that the reference sign [7A] in FIG. 7 shows a top view viewed in the direction of the arrow [A] in FIG. 6. The reference sign [7B] in FIG. 7 shows a side view viewed in the direction of the arrow [B] in FIG. 6. The reference sign [7C] in FIG. 7 shows a bottom view viewed in the direction of the arrow [C] in FIG. 6. FIG. 8 is a cross-sectional view taken along the line [8]-[8] in FIG. 6. Each of FIG. 9 and FIG. 10 is a view conceptually showing an optical axis adjusting process when incorporating the image pickup unit of the present embodiment into the distal end portion of the insertion portion of the endoscope. FIG. 9 is a plan view of the image pickup unit when viewed from the top surface side. FIG. 10 is a front view of the image pickup unit in FIG. 9 when viewed in a direction corresponding to the arrow [D] in FIG. 6.

Basic configuration of the present embodiment is substantially the same as that of the above-described first embodiment. Therefore, in the description below, components which are the same as those in the first embodiment are attached with the same reference signs and detailed description thereof will be omitted, and only a part different from that of the first embodiment will be described in detail.

An image pickup unit 20B of the present embodiment, as shown in the drawings, is different in that a second electric substrate 22B has a flange 22Bf. The flange 22Bf contributes to define the direction of the optical axis O of the image pickup optical system 25 to a predetermined direction when the image pickup unit 20B is incorporated into the distal end portion of the insertion portion of the endoscope.

In general, when the image pickup unit is incorporated in the distal end portion of the insertion portion of the endoscope, the optical axis O of the image pickup optical system has to be set in the defined direction. The direction of the optical axis O of the image pickup optical system defines an acquisition range of an observation image that is acquired by the image pickup device. Therefore, if the direction of the optical axis O of the image pickup optical system is inclined or biased with respect to the defined direction, the acquisition range of the observation image differs for each of the manufactured endoscopes. In addition, if the observation image differs for each of the endoscopes, in a case where a plurality of endoscopes are used, there is a possibility that the difference affects the operability of each of the endoscopes. In view of the possibility, when the image pickup unit is incorporated into the distal end portion of the insertion portion of the endoscope, the direction of the optical axis O of the image pickup unit has to be adjusted with high accuracy in accordance with the defined direction.

To this end, in the image pickup unit 20B of the present embodiment, the flange 22Bf is provided on the outer circumferential surface of the second electric substrate 22B. By providing the flange 22Bf, it is easily to perform position adjustment of the optical axis O of the image pickup optical system 25 in the image pickup unit 20B of the present embodiment.

In this case, at least one plane of the flange 22Bf is formed in parallel with the image pickup device mounting surface 21a of the first electric substrate 21. Here, the above-described one plane is referred to as a position restricting surface 22Bfa. Note that also another plane 22Bfb of the flange 22Bf, which is opposing to the position restricting surface 22Bfa, is similarly formed in parallel with the image pickup device mounting surface 21a of the first electric substrate 21.

The flange 22Bf is disposed so as to surround the outer circumferential surface of the second electric substrate 22B. However, the flange 22Bf is not provided over the entire circumference of the second electric substrate 22B, but has a cutout portion 22Bfc formed by a part of the flange in the circumferential direction being cut. The cutout portion 22Bfc is a part in which a part of the conductive circuit 26 is disposed. In other words, the flange 22Bf is provided at such a position as to avoid the part of the conductive circuit 26 disposed on the first surface 22c of the second electric substrate 22B.

The reason why the flange 22Bf is thus configured by including the cutout portion 22Bfc will be described below. In the case where the solid electric substrate 23 is formed by an MID, for example, if the flange 22Bf is provided over the entire circumference of the second electric substrate 22B, a part of the conductive circuit 26 is disposed along the outer surface side of the flange 22Bf.

However, the flange 22Bf, although details thereof will be described later, has a contact surface (position restricting surface 22Bfa to be described later; see FIG. 9 and FIG. 10)

configured to contact a fixed part on the endoscope side. If a part of the conductive circuit 26 is provided on the contact surface (position restricting surface 22Bfa), the part of the conductive circuit 26 is sandwiched between the contact surface and the fixed part on the endoscope side, when the image pickup unit 20B is incorporated into the distal end portion of the insertion portion of the endoscope. At this time, there is a possibility that the conductive circuit 26 is damaged. Such a damage causes an electrical loss, which leads to degradation in the transmission quality.

In view of the above, in the image pickup unit 20B of the present embodiment, the flange 22Bf of the second electric substrate 22B is formed to include the cutout portion 22Bfc for avoiding the conductive circuit 26. Then, the conductive circuit 26 is passed through the cutout portion 22Bfc, to thereby prevent the conductive circuit 26 from contacting the fixed part on the endoscope side.

In accordance with the position restricting surface 22Bfa provided to the flange 22Bf, the endoscope to which the image pickup unit 20B of the present embodiment is applied includes, in the distal end portion of the insertion portion, an image pickup unit holding portion 30 (see FIG. 9 and FIG. 10) as a part of a fixing member configured to hold the image pickup unit 20B.

The image pickup unit holding portion 30, as shown in FIG. 9 and FIG. 10, is a fixing member which covers at least a part of the outer circumferential surface of the second electric substrate 22B of the image pickup unit 20B in the state incorporated in the distal end portion of the insertion portion, and which includes a housing portion 30c in which a part of the second electric substrate 22B is arranged. The image pickup unit holding portion 30 includes a flange contact surface 30a with which the position restricting surface 22Bfa comes into contact is formed at a position facing the position restricting surface 22Bfa of the flange 22Bf of the image pickup unit 20B incorporated in the distal end portion of the insertion portion of the endoscope. The flange contact surface 30a is set such that the optical axis O of the image pickup optical system 25 is directed in a defined direction when the position restricting surface 22Bfa of the flange 22Bf contacts the flange contact surface 30a. As described above, the direction of the optical axis O defines the acquisition range of the observation image to be acquired by the image pickup device 24. Therefore, setting the direction of the optical axis O of the image pickup optical system 25 means setting the acquisition range of the observation image acquired by the endoscope.

With such a configuration, when the image pickup unit 20B is incorporated into the distal end portion of the insertion portion of the endoscope, the position restricting surface 22Bfa of the flange 22Bf is directed in the direction of the arrow Z in FIG. 10 and brought into contact with the flange contact surface 30a. Then, this enables the direction of the optical axis O of the image pickup optical system 25 in the image pickup unit 20B to be easily set to the defined direction.

In addition, in the state where the position restricting surface 22Bfa of the flange 22Bf of the image pickup unit 20B is brought into contact with the flange contact surface 30a of the image pickup unit holding portion 30, a clearance CL is formed between the outer circumferential surface of the second electric substrate 22B and an inner wall surface 30b of the image pickup unit holding portion 30. By forming the clearance CL, when the image pickup unit 20B is arranged at a predetermined position with respect to the image pickup unit holding portion 30, the position adjustment of the image pickup unit 20B in a surface in the vertical direction with respect to the optical axis O of the image pickup optical system 25 can be performed, while maintaining the state where the image pickup unit 20B is arranged at the predetermined position.

Such a configuration enables the image pickup unit 20B to move in the vertical direction with respect to the optical axis O within a range of the clearance CL, while maintaining the state where the position restricting surface 22Bfa of the flange 22Bf of the image pickup unit 20B is in contact with the flange contact surface 30a of the image pickup unit holding portion 30. Thus, it is possible to simultaneously perform the position adjustment of the image pickup unit 20B in the surface in the vertical direction with respect to the optical axis O.

Furthermore, in the image pickup unit 20B of the present embodiment, the second electric substrate 22B is formed such that at least a part thereof has an arc shape (substantially circular shape) when viewed in the cross section in the vertical direction with respect to the optical axis O. The shape of the second electric substrate 22B of the image pickup unit 20B is formed in such a shape, to thereby enable the image pickup unit 20B to rotate around the optical axis O, when the image pickup unit 20B is arranged at the predetermined position with respect to the image pickup unit holding portion 30.

Thus, after adjusting the direction of the optical axis O and the position of the image pickup optical system 25 as described above, the image pickup unit 20B is rotated in the direction of the arrow R in FIG. 10, while maintaining the state where the direction of the optical axis O and the position have been adjusted, and thereby it is possible to easily adjust the position of the image pickup unit 20B in the rotation direction. At the time of adjusting the position in the rotation direction, it is preferable to maintain the state where the position restricting surface 22Bfa of the flange 22Bf is in contact with the flange contact surface 30a of the image pickup unit holding portion 30. To this end, for example, a pressing jig 31 (see FIG. 10) and the like is used. The pressing jig 31 is configured to press the image pickup unit 20B against the image pickup unit holding portion 30 in the Z direction in FIG. 10.

With such a configuration, it is possible to surely adjust the position of the image pickup unit 20B, that is, the position of the image pickup unit 20B in the rotation direction, while preventing the optical axis O of the image pickup optical system 25 from displacing in the surface in the Z direction and in the surface in the vertical direction with respect to the Z direction.

After adjusting the position of the optical axis O of the image pickup optical system 25 in the image pickup unit 20B, in order to fix the adjusted state, the image pickup unit 20B is fixed to the image pickup holding portion 30 by using an adhesive or the like. Other configurations are the same as those in the above-described first embodiment.

As described above, the second embodiment is capable of obtaining substantially the same effects as those in the first embodiment.

In addition, according to the second embodiment, the image pickup unit 20B is configured such that the second electric substrate 22B includes the flange 22Bf. In accordance with such a configuration, on the side of the endoscope applying the image pickup unit 20B, the image pickup unit holding portion 30 including the flange contact surface 30a corresponding to the flange 22Bf is provided.

The configuration enables various kinds of position adjustment of the image pickup unit 20B to be performed easily and simultaneously when the image pickup unit 20B is incorporated into the distal end portion of the insertion portion of the endoscope. As a result, the configuration is capable of simplifying the assembling process, and contributing to the reduction of the assembling time and also to the reduction of the manufacturing cost.

Note that, in the image pickup unit 20B of the above-described second embodiment, as an example, the second electric substrate 22B of the solid electric substrate 23B is configured such that the second electric substrate 22B has the substantially circular shape when viewed in the cross section in the vertical direction with respect to the optical axis O. However, the image pickup unit according to the present invention is not limited to the above-described configuration example.

In the image pickup unit according to the present invention, the second electric substrate in the solid electric substrate may have a different configuration as long as at least a part of the second electric substrate has an arc shape when viewed in the cross section in the vertical direction with respect to the optical axis O. The second electric substrate may have the shape as shown in FIG. 11, for example.

Figure 11:
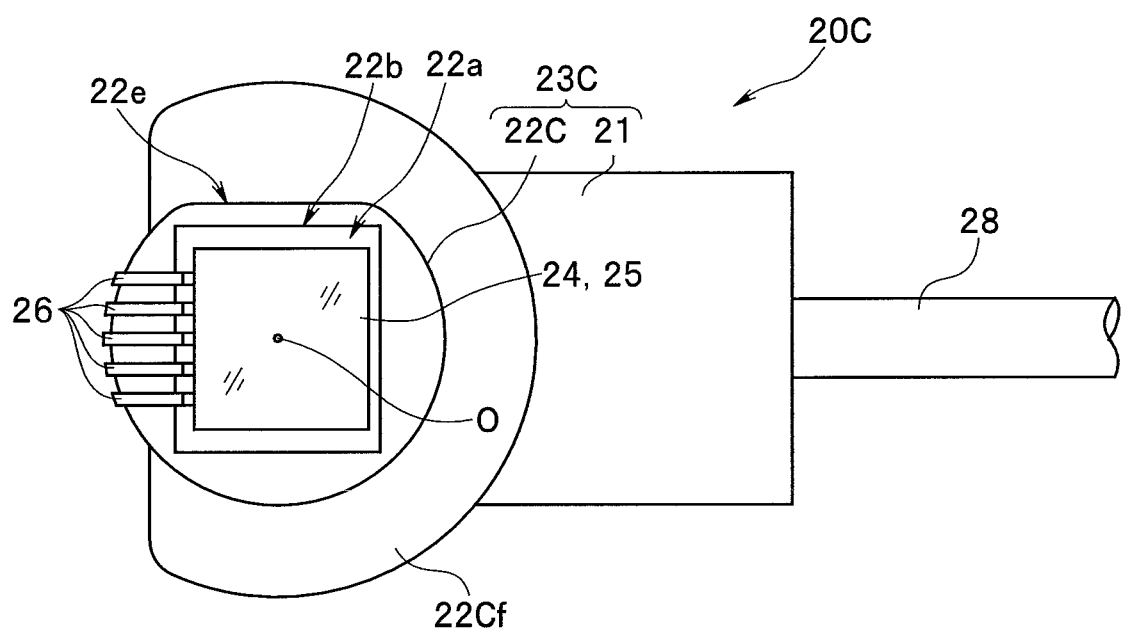
FIG. 11 shows a modification of the image pickup unit of the second embodiment of the present invention, and is a plan view of the image pickup unit when viewed from a top surface.

FIG. 11 is a view showing a modification of the image pickup unit of the above-described second embodiment. FIG. 11 is a plan view of the image pickup unit of the modification when viewed from the top surface. As shown in FIG. 11, the solid electric substrate 23C in an image pickup unit 20C of the modification is configured such that a second electric substrate 22C has a substantially circular shape as a whole when viewed in the cross section in the vertical direction with respect to the optical axis O. and the second electric substrate 22C includes a cutout portion 22e formed by a part of the outer circumference of the second electric substrate 22C being cut. The second electric substrate 22C includes, on the outer circumferential surface thereof, a flange 22Cf. Other configurations are the same as those of the above-described image pickup unit 20B.

Even if the second electric substrate 22C thus configured is employed, it is possible to obtain exactly the same effects as those in the above-described second embodiment.

Incidentally, in conventional arts, in order to fix and hold an image pickup unit in a distal end portion of an insertion portion of an endoscope, it has been common to fix the image pickup unit to a fixing member (for example, the part referred to as an image pickup unit holding portion, or the like) in the distal end portion of the insertion portion of the endoscope by using an adhesive or the like.

However, in recent years, an adhesion area for adhering the image pickup unit and an inner fixing member tends to decrease with miniaturization of an endoscope and an image pickup unit, which leads to a tendency of degradation in durability when adhering and fixing the image pickup unit.

Therefore, if an unintended shock force or the like is applied from outside to a distal end portion of an insertion portion of an endoscope by the endoscope being fallen on a floor surface, for example, during the use or transportation of the endoscope, there might be a possibility that adhering and fixing of an inner structure such as an image pickup unit come off and the inner structure falls off in the distal end portion of the insertion portion of the endoscope.

In view of the above, the endoscope applying the image pickup unit 20B of the above-described second embodiment is provided with a configuration to be described below, to thereby improve a force for fixing and holding the image pickup unit in the distal end portion of the insertion portion of the endoscope. Hereinafter, a configuration example for the fixing and holding of the image pickup unit will be described with reference to FIGS. 12 to 19.

Figure 12:
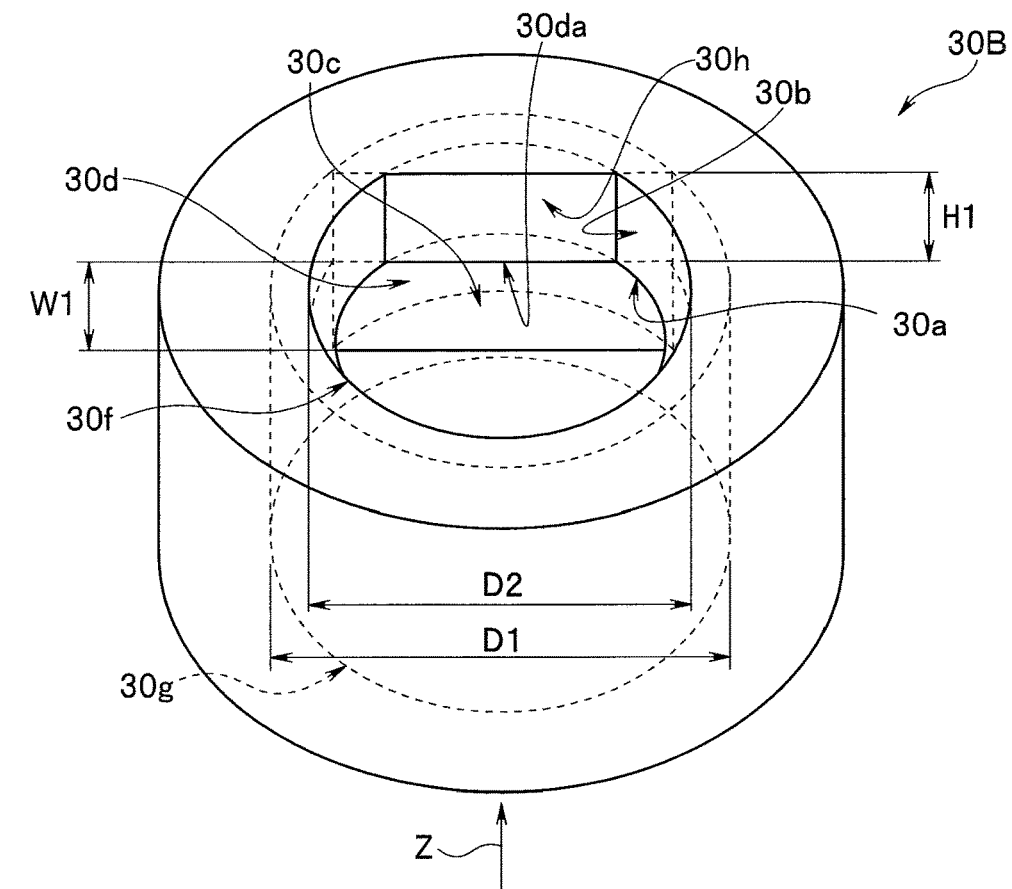
FIG. 12 is a schematic perspective view showing a configuration of the image pickup unit of the second embodiment of the present invention and a configuration of an image pickup unit holding portion in the endoscope applying the image pickup unit.
Figure 12:
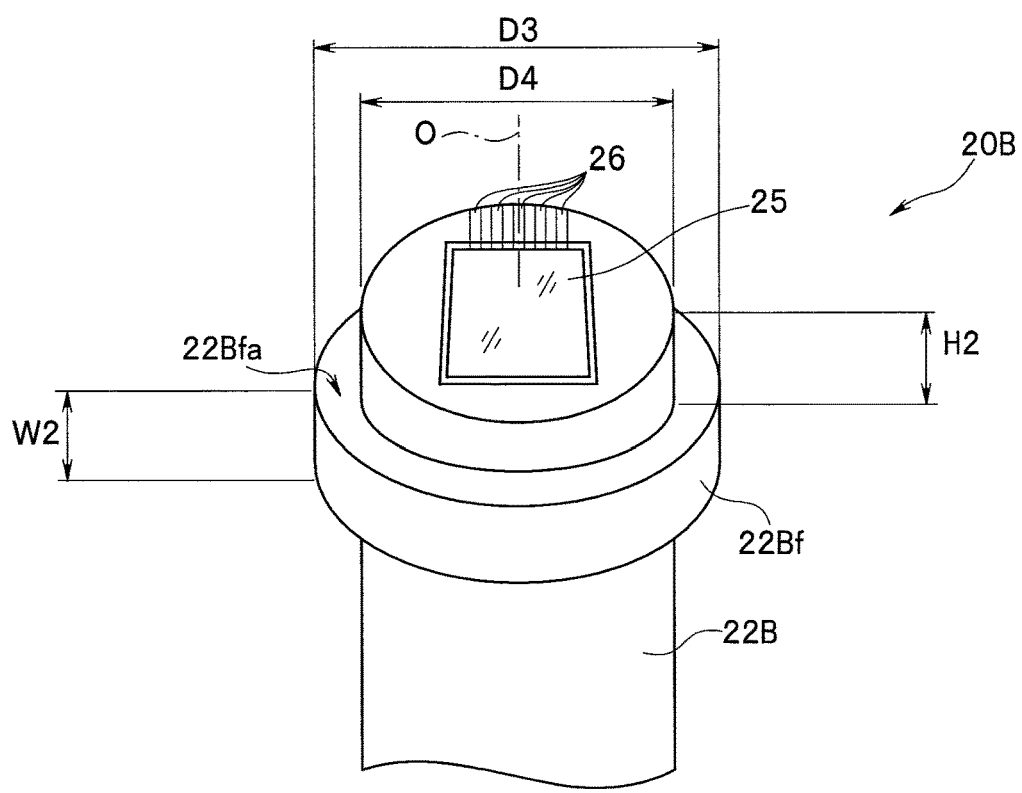
Figure 13:
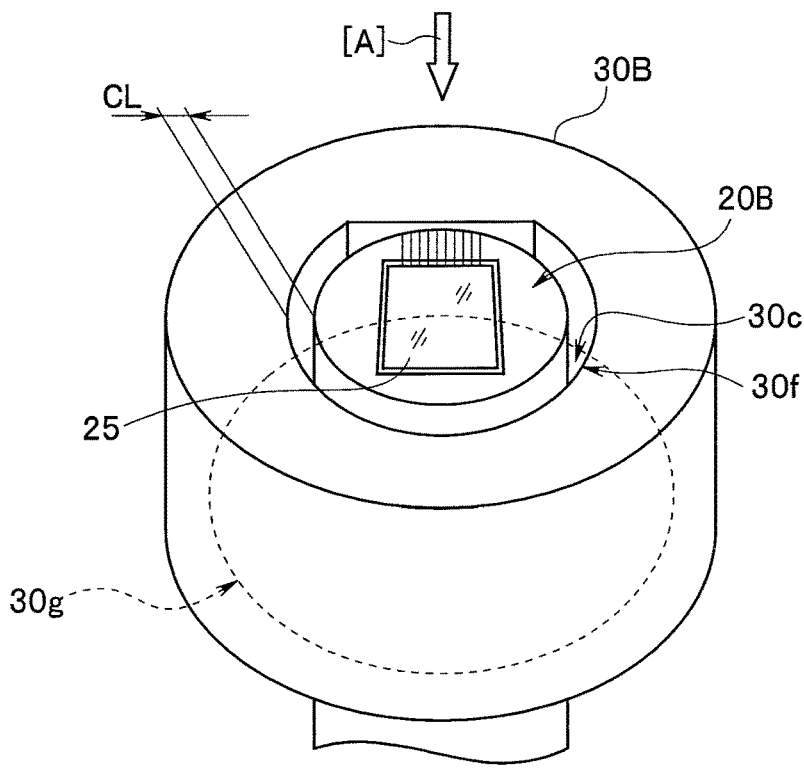
FIG. 13 is a schematic view showing a state where the image pickup unit in FIG. 12 is incorporated in the image pickup unit holding portion in FIG. 12.
Figure 14:
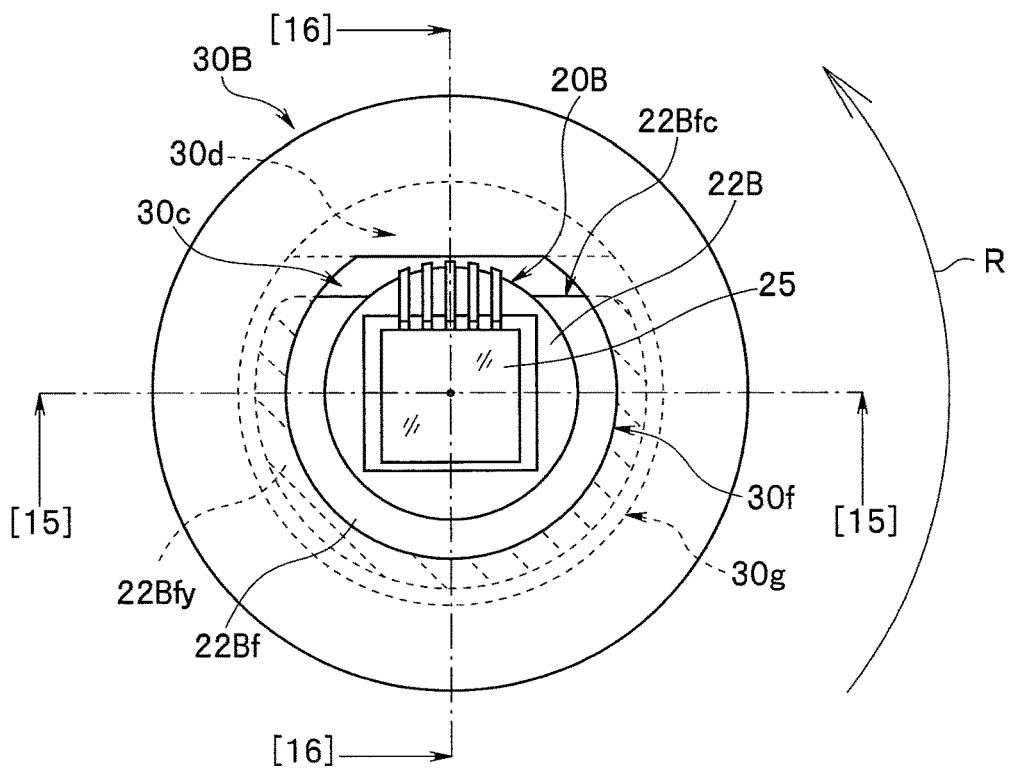
FIG. 14 is a top view when viewed in a direction of the arrow [A] in FIG. 13.
Figure 15:
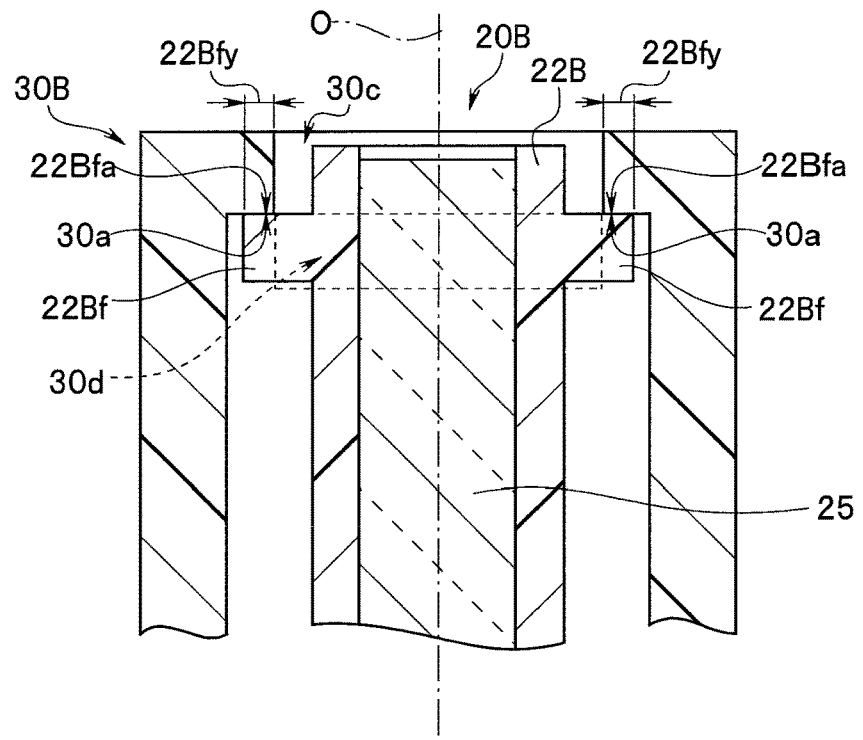
FIG. 15 is a schematic view showing a cross section taken along the line [15]-[15] in FIG. 14.
Figure 16:
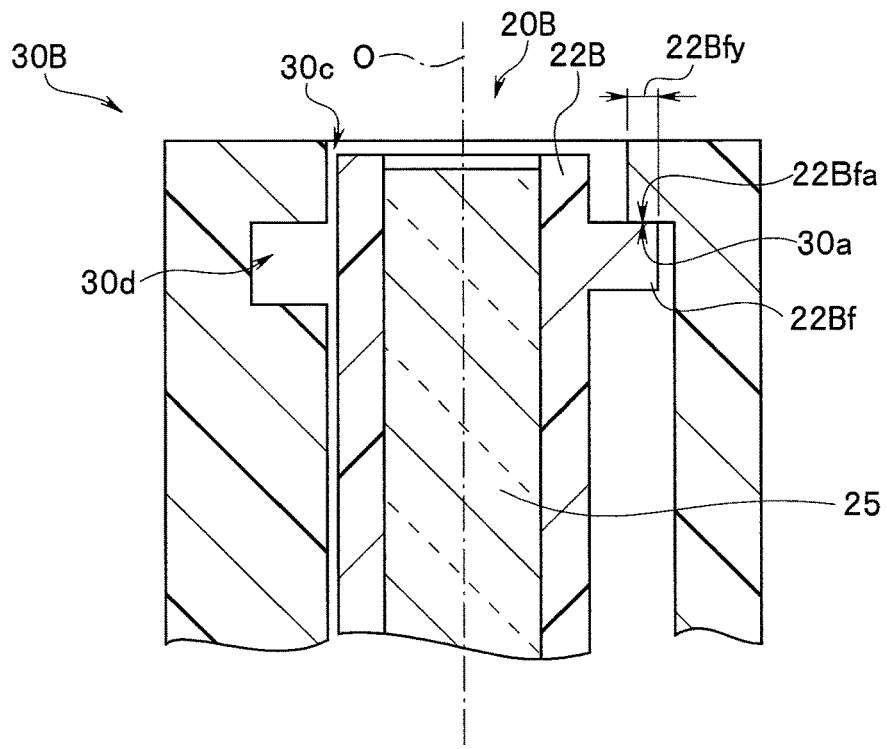
FIG. 16 is a schematic view showing a cross section taken along the line [16]-[16] in FIG. 14.
Figure 17:
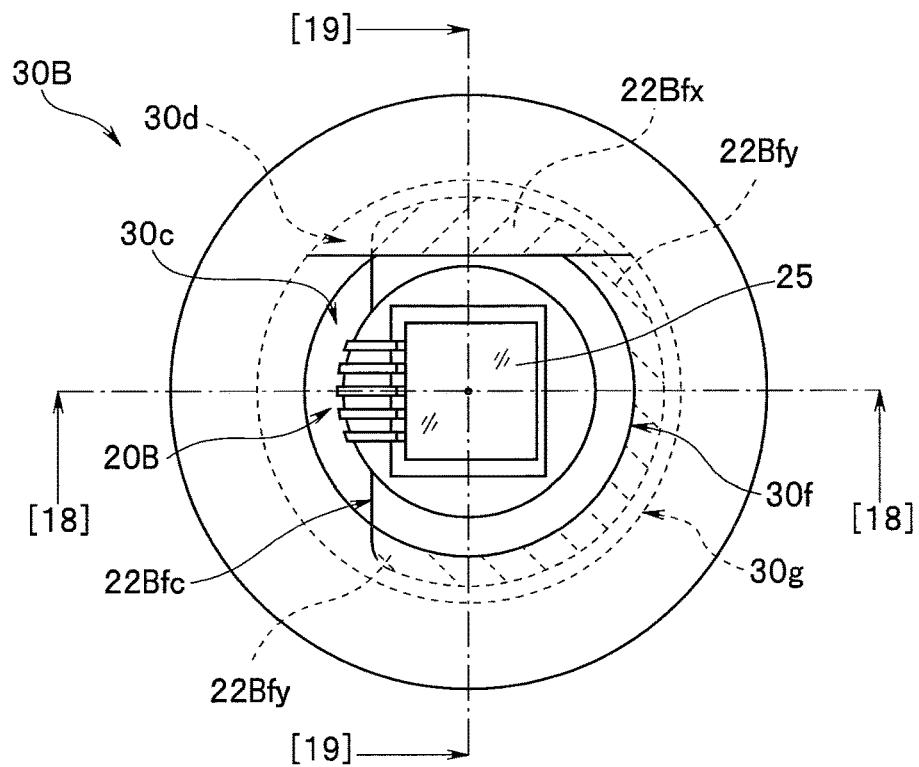
FIG. 17 is a top view showing a state after the image pickup unit in the state in FIG. 14 has been rotated in a predetermined direction by a predetermined rotation angle.
Figure 18:
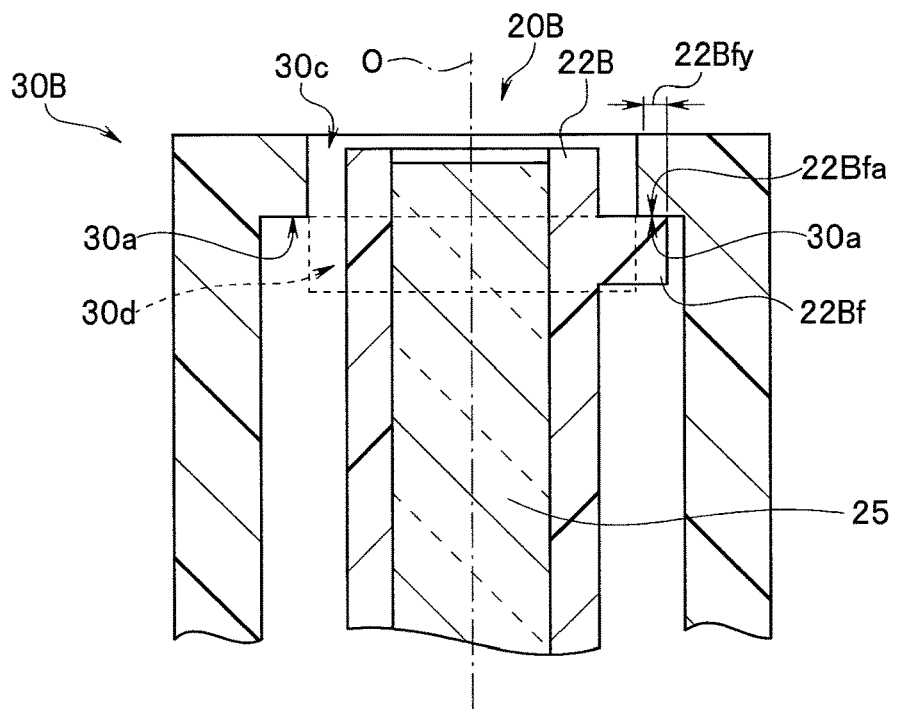
FIG. 18 is a schematic view showing a cross section taken along the line [18]-[18] in FIG. 17.
Figure 19:
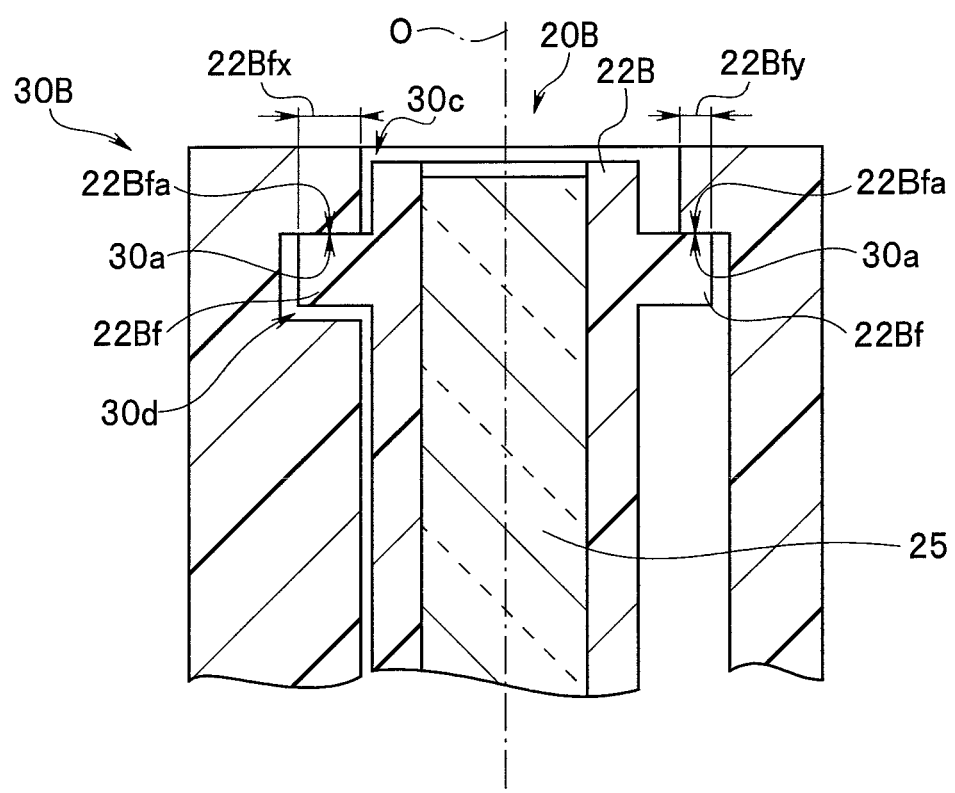
FIG. 19 is a schematic view showing a cross section taken along the line [19]-[19] in FIG. 17.

FIGS. 12 to 19 are views each conceptually showing a configuration example for the fixing and holding of the image pickup unit in the endoscope applying the image pickup unit of the second embodiment of the present invention. Among these figures, FIG. 12 is a schematic perspective view showing a configuration of the image pickup unit of the present embodiment and a configuration of the image pickup unit holding portion in the endoscope applying the image pickup unit. FIG. 13 is a schematic view showing the state where the image pickup unit in FIG. 12 is incorporated in the image pickup unit holding portion in FIG. 12. FIG. 14 is a top view when viewed in the direction of the arrow [A] in FIG. 13. FIG. 15 is a schematic view showing a cross section taken along the line [15]-[15] in FIG. 14. FIG. 16 is a schematic view showing a cross section taken along the line [16]-[16] in FIG. 14. FIG. 17 is a top view showing a state after the image pickup unit in the state in FIG. 14 has been rotated in a predetermined direction by a predetermined rotation angle. FIG. 18 is a schematic view showing a cross section taken along the line [18]-[18] in FIG. 17. FIG. 19 is a schematic view showing a cross section taken along the line [19]-[19] in FIG. 17.

The image pickup unit 20B applied in the present configuration example is the same as the one described with reference to the above-described FIGS. 6 to 10. Therefore, the configuration of the image pickup unit 20B itself is the same as that described above.

An image pickup unit holding portion 30B shown in each of FIGS. 12 to 19 is conceptually shown by taking out a part of the fixing member in the distal end portion of the insertion portion of the endoscope. In addition, in each of FIGS. 12 to 19, the image pickup unit 20B is shown by taking out a part thereof. In this case, showing a part of the image pickup unit 20B indicates that a predetermined part of the second electric substrate 22B to be engaged with the image pickup unit holding portion 30B is mainly illustrated and illustration of other parts is omitted.

The image pickup unit holding portion 30B in the present configuration example is formed so as to be adapted to the image pickup unit 20B of the above-described second embodiment. The image pickup unit holding portion 30B in the present configuration example is formed, in substantially the same manner as the image pickup unit holding portion 30 described in the above-described second embodiment, so as to cover at least a part of the outer circumferential surface of the second electric substrate 22B of the image pickup unit 20B incorporated in the distal end portion of the insertion portion of the endoscope, and the image pickup unit holding portion 30B includes a housing portion 30c in which the distal end part of the second electric substrate 22B is arranged.

On the distal end side of the housing portion 30c, a distal end opening 30f (see FIG. 12 and FIG. 13) that is open toward outside is formed. In the distal end opening 30f, the distal end part of the second electric substrate 22B in the image pickup unit 20B, that is, the front surface part of the image pickup optical system 25 is arranged (see FIG. 13).

In addition, in the housing portion 30c, on the surface opposing to the distal end opening 30f, an insertion side opening 30g (see FIG. 12 and FIG. 13) that is open toward outside is formed. The insertion side opening 30g is an opening through which the distal end part of the second electric substrate 22B of the image pickup unit 20B is inserted along the direction of the arrow Z shown in FIG. 12, in assembling the image pickup unit 20B to the image pickup unit holding portion 30B. The distal end opening 30f and the insertion side opening 30g communicate with each other inside the housing portion 30c.

Each of the distal end opening 30f and the insertion side opening 30g is formed in a substantially circular shape having a cutout surface 30h (see FIG. 12) formed by cutting a part of each of the openings. Each of the distal end opening 30f and the insertion side opening 30g is formed to have a different inner diameter size. The inner diameter size (reference sign D2 in FIG. 12) of the distal end opening 30f is set to be smaller than the inner diameter size (reference sign D1 in FIG. 12) of the insertion side opening 30g (D1>D2).

As described above, the distal end part of the second electric substrate 22B in the image pickup unit 20B is arranged in the distal end opening 30f. At this time, the front surface of the image pickup optical system 25 is exposed outside from the distal end opening 30f. The distal end opening 30f is formed to have the diameter having a size enough for allowing at least the front surface of the image pickup optical system 25 to expose outside.

In addition, the distal end opening 30f is formed to have a diameter size smaller than the outer diameter size of the flange 22Bf of the second electric substrate 22B. Such a configuration prevents the distal end part of the second electric substrate 22B from protruding outside from the distal end opening 30f.

Note that, as shown in FIG. 13, a predetermined clearance CL is formed between the outer circumferential side surface of the distal end part of the second electric substrate 22B of the image pickup unit 20B incorporated in the distal end portion of the insertion portion of the endoscope and the inner wall surface 30b of the image pickup unit holding portion 30B side, the inner wall surface 30b facing the outer circumferential side surface.

In addition, the image pickup unit holding portion 30B includes the flange contact surface 30a with which the position restricting surface 22Bfa of the flange 22Bf of the image pickup unit 20B comes into contact, at a position facing the position restricting surface 22Bfa when the distal end part of the second electric substrate 22B is arranged in the housing portion 30c. The flange contact surface 30a is formed over the substantially entire circumference of the housing portion 30c along the circumferential direction of the inner wall surface 30b of the housing portion 30c. However, the flange contact surface 30a is not provided at the part corresponding to the cutout surface 30h (see FIG. 12). The flange contact surface 30a is formed in parallel with the distal end surface of the image pickup holding portion 30B at a position separated from the distal end surface of the image pickup unit holding portion 30B by a predetermined distance H1 (see FIG. 12) in the direction of the optical axis O. Here, the predetermined distance is set to be substantially equal to a distance (see the reference sign H2 in FIG. 12) from the front surface of the image pickup optical system 25 to the position restricting surface 22Bfa of the flange 22Bf in the direction of the optical axis O in the second electric substrate 22B of the image pickup unit 20B.

With such a configuration, when the image pickup unit 20B is incorporated into the image pickup unit holding portion 30B, if the position restricting surface 22Bfa of the flange 22Bf is brought into contact with the flange contact surface 30a, the image pickup unit 20B can be arranged at a predetermined position where the front surface of the image pickup optical system 25 in the second electric substrate 22B does not protrude outward and the front surface of the image pickup optical system 25 is substantially flush with the distal end surface of the image pickup unit holding portion 30B.

In the vicinity of the cutout surface 30h, a key groove 30d is provided. The key groove 30d is formed from the inner wall surface 30b so as to have a semicircular concave shape. An upper side surface 30da (see FIG. 12) of the key groove 30d is formed to be connected to the flange contact surface 30a. A width size (W1; see FIG. 12) of the key groove 30d in the direction (Z direction) along the optical axis O is set to be larger than a thickness size (W2; see FIG. 12) of the flange 22Bf of the second electric substrate 22B (W1>W2).

With such a configuration, when the image pickup unit 20B is incorporated into the image pickup unit holding portion 30B, if the position restricting surface 22Bfa of the flange 22Bf is brought into contact with the flange contact surface 30a, and the image pickup unit 20B is rotated around the optical axis O by a predetermined rotation amount while maintaining the contacting state, the flange 22Bf is engaged with the key groove 30d. In the state, if the image pickup unit 20B is adhered and fixed, the image pickup unit 20B can be fixed more firmly in the direction along the optical axis O.

Note that the reference sign D1 in FIG. 12 indicates the inner diameter size of the insertion side opening 30g of the image pickup unit holding portion 30B. The reference sign D2 in FIG. 12 indicates the inner diameter size of the distal end opening 30f of the image pickup unit holding portion 30B. The reference sign D3 in FIG. 12 indicates the outer diameter size of the flange 22Bf of the second electric substrate 22B. The reference sign D4 in FIG. 12 indicates the outer diameter size of the distal end part of the second electric substrate 22B.

Here, the outer diameter size D3 of the flange 22Bf of the second electric substrate 22B is larger than the outer diameter size D4 of the distal end part of the second electric substrate 22B (D3>D4). The inner diameter size D1 of the insertion side opening 30g of the image pickup unit holding portion 30B is larger than the outer diameter size D3 of the flange 22Bf of the second electric substrate 22B (D1>D3). The outer diameter size D3 of the flange 22Bf of the second electric substrate 22B is larger than the inner diameter size D2 of the distal end opening 30f of the image pickup unit holding portion 30B (D3>D2).

The inner diameter size D2 of the distal end opening 30f of the image pickup unit holding portion 30B is larger than the outer diameter size D4 of the distal end part of the second electric substrate 22B (D2>D4). Thus, the respective diameter sizes are set to have the following relation.

$$D1 > D3 > D2 > D4$$

With such a configuration, the distal end part of the second electric substrate 22B can be inserted from the insertion side opening 30g in the direction of the arrow Z in FIG. 12. When the position restricting surface 22Bfa of the flange 22Bf contacts the flange contact surface 30a, the second electric substrate 22B is arranged at the predetermined position. At this time, the distal end part of the second electric substrate 22B is arranged at the predetermined position in the distal end opening 30f, with the front surface of the image pickup optical system 25 not protruding outside from the image pickup unit holding portion 30B.

The working of the present configuration example thus configured will be described below.

First, as shown in FIG. 12, the distal end part of the second electric substrate 22B of the image pickup unit 20B is inserted from the insertion side opening 30g of the image pickup unit holding portion 30B in the direction of the arrow Z. At the time of the insertion, the cutout portion 22Bfc of the flange 22Bf of the image pickup unit 20B is brought into a state facing the cutout surface 30h of the image pickup unit holding portion 30B. The reason is that, in a state other than the above-described state, the flange 22Bf is caught by the insertion side opening 30g and the image pickup unit 20B cannot be inserted from the insertion side opening 30g.

Then, the position restricting surface 22Bfa of the flange 22Bf contacts the flange contact surface 30a. At this time, the image pickup unit 20B is arranged at the predetermined position at which the front surface of the image pickup optical system 25 of the image pickup unit 20B and the distal end surface of the image pickup unit holding portion 30B are substantially flush with each other. The state at this time is shown in FIGS. 13 to 16.

In the state, the position restricting surface 22Bfa of the flange 22Bf contacts the flange contact surface 30a in the state as shown in FIG. 14. In other words, a region 22Bfy shown by the leftward dot oblique lines in FIG. 14 is a region in which the position restricting surface 22Bfa of the flange 22Bf contacts the flange contact surface 30a. Note that, at this time, the flange 22Bf is not engaged with the key groove 30d.

In this state, the image pickup unit 20B is rotated in the direction of the arrow R shown in FIG. 14 (in the counter-clockwise direction in FIG. 14) by an angle of substantially 90 degrees. Then, the state of the image pickup unit 20B is shifted to the state shown in FIGS. 17 to 19.

When the image pickup unit 20B is shifted to the state, the position restricting surface 22Bfa of the flange 22Bf contacts the flange contact surface 30a in the state as shown in FIG. 17. In other words, a region 22Bfy shown by the leftward dot oblique lines in FIG. 17 is a region in which the position restricting surface 22Bfa of the flange 22Bf contacts the flange contact surface 30a.

In addition, at this time, a part of the flange 22Bf is engaged with the key groove 30d. A part of the position restricting surface 22Bfa of the flange 22Bf is in contact with the upper side surface of the key groove 30d. In other words, a region 22Bfx shown by the rightward dot oblique lines in FIG. 17 is a region in which a part of the position restricting surface 22Bfa of the flange 22Bf is in contact with the upper side surface of the key groove 30d.

When the part of the flange 22Bf is thus engaged with the key groove 30d, movement of the image pickup unit 20B in the direction along the optical axis O is restricted. In this state, even in a case where an unintended shock force or the like is applied from outside, for example, the image pickup unit 20B is prevented from coming off from the housing portion 30c of the image pickup unit holding portion 30B.

After performing various kinds of adjustment on the image pickup unit 20B with the part of the flange 22Bf being engaged with the key groove 30d, the image pickup unit 20B is adhered and fixed to the image pickup unit holding portion 30B with an adhesive or the like.

As described above, by applying the above-described configuration example to the endoscope applying the image pickup unit 20B of the second embodiment, it is possible to obtain substantially the same effects as those in the above-described respective embodiments.

Furthermore, in the present configuration example, the image pickup unit holding portion 30B includes the key groove 30d. In addition, the flange 22Bf of the image pickup unit 20B is configured such that, when the image pickup unit 20B is incorporated in the predetermined position of the image pickup unit holding portion 30B, a part of the flange 22Bf of the image pickup unit 20B is engaged with the key groove 30d. With such a configuration, the image pickup unit 20B can be fixed more firmly in the distal end portion of the insertion portion of the endoscope.

Figure 20:
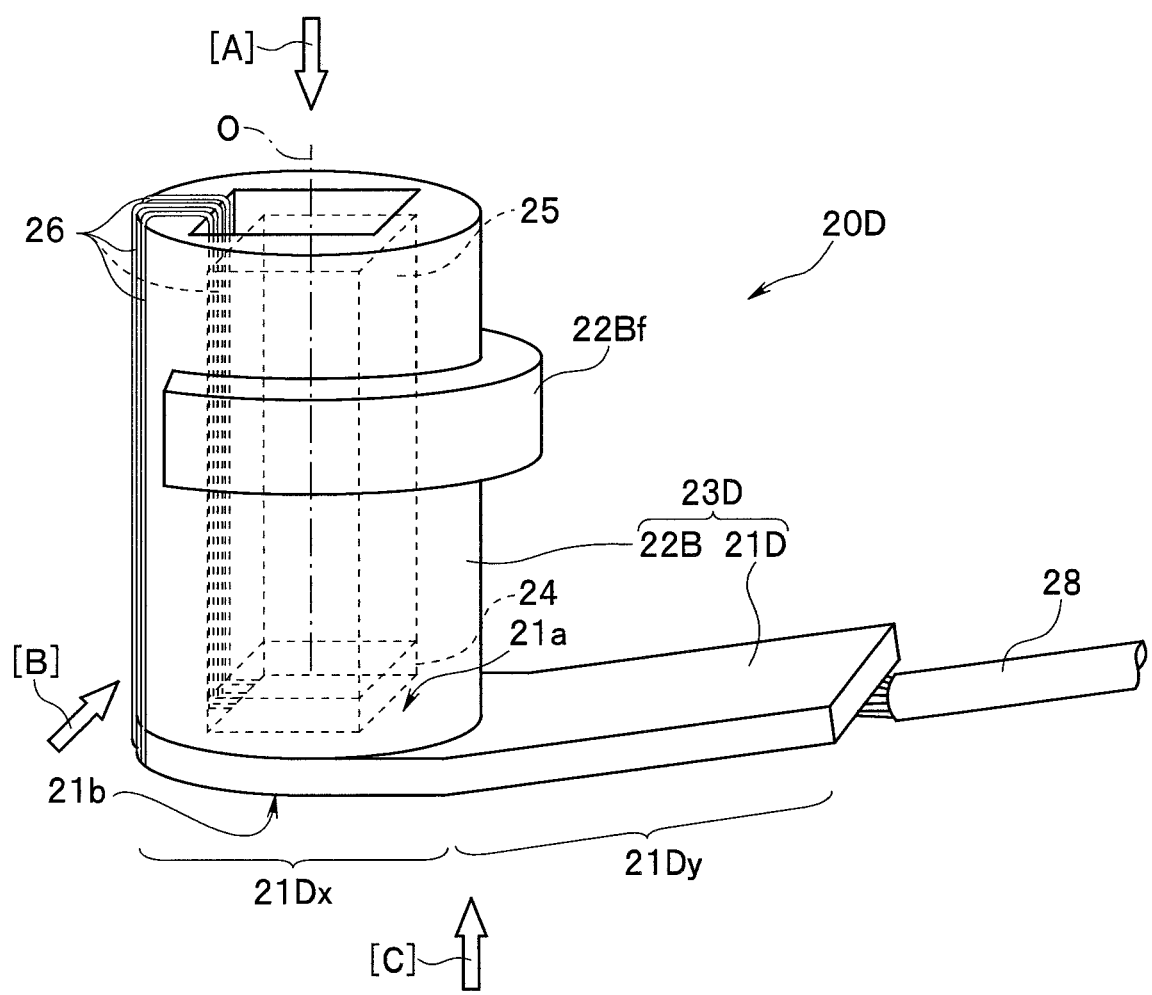
FIG. 20 is a perspective view conceptually showing an exterior of an image pickup unit of a third embodiment of the present invention.
Figure 21:
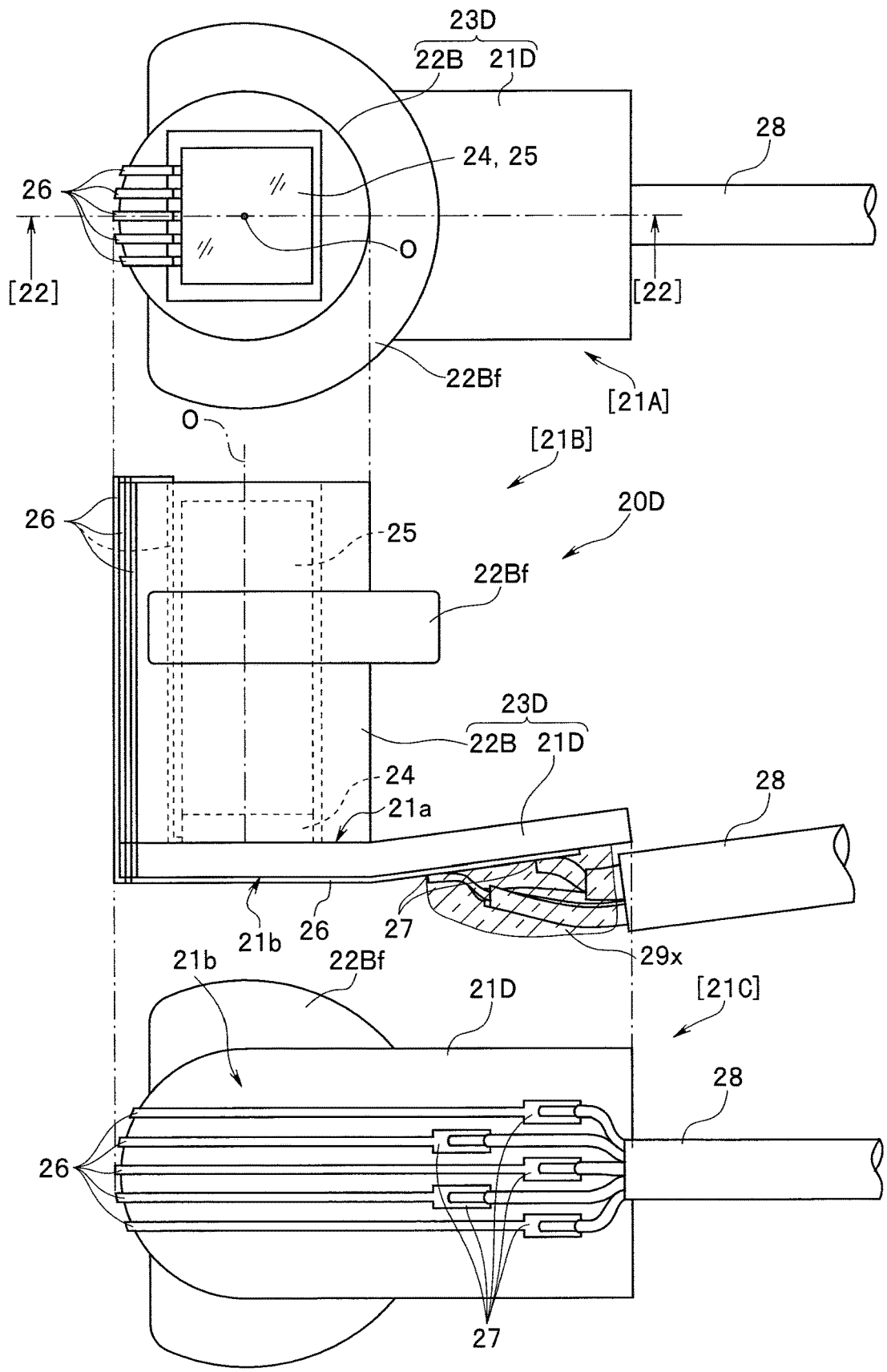
FIG. 21 is a trihedral view of the image pickup unit of the third embodiment of the present invention.
Figure 22:
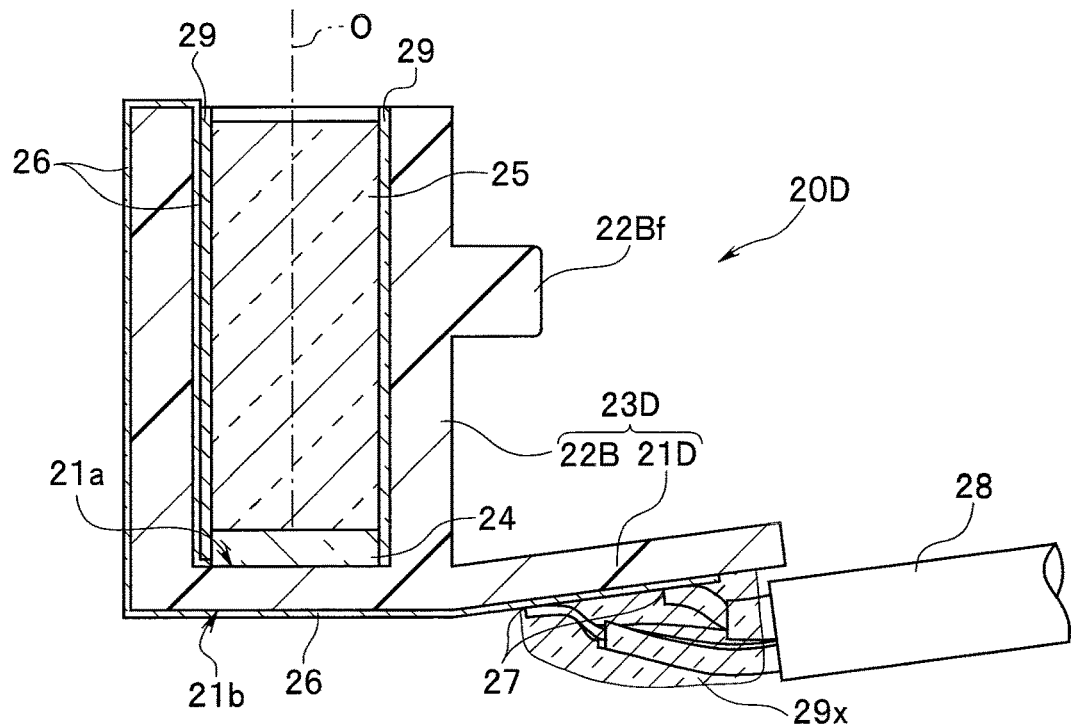
FIG. 22 is a cross-sectional view taken along the line [22]-[22] in FIG. 21.
Figure 23:
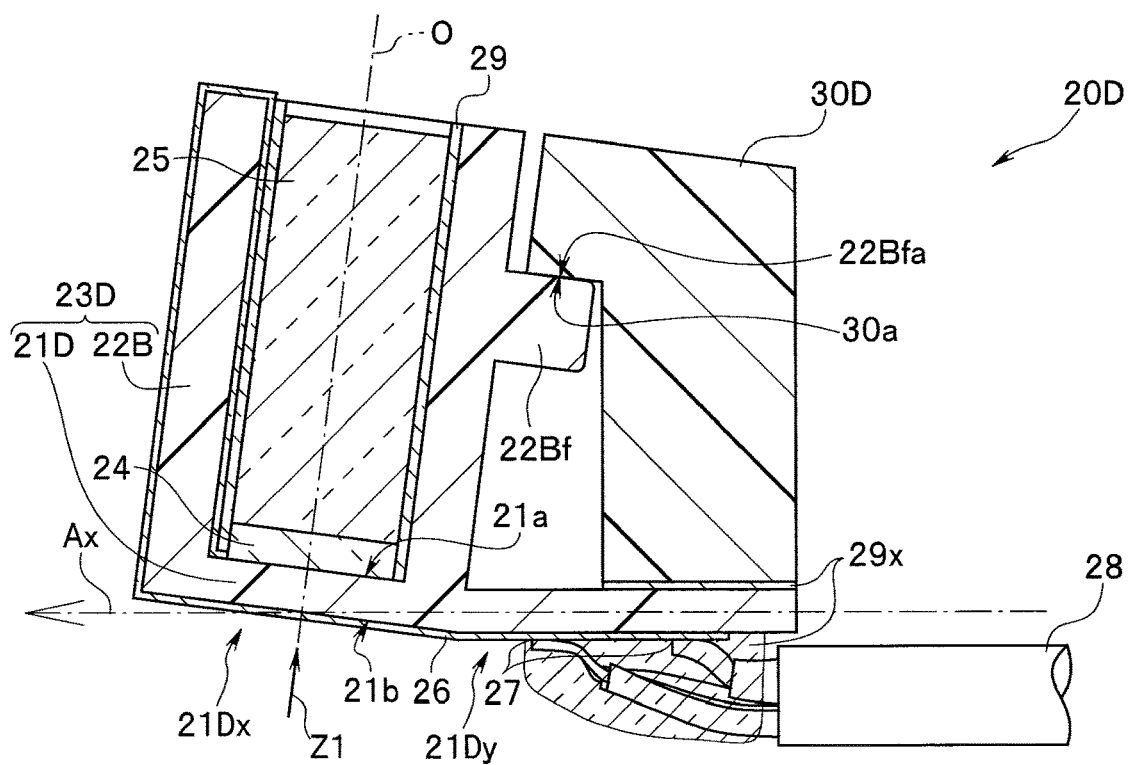
FIG. 23 is a cross-sectional view conceptually showing a state where the image pickup unit shown in FIG. 20 is held by an image pickup unit holding portion.

Next, an image pickup unit of a third embodiment of the present invention will be described below with reference to FIGS. 20 to 23. FIG. 20 is a perspective view conceptually showing an exterior of the image pickup unit of the third embodiment of the present invention. FIG. 21 is a trihedral view of the image pickup unit of the present embodiment. Note that the reference sign [21A] in FIG. 21 shows a top view viewed in the direction of the arrow [A] in FIG. 20. The reference sign [21B] in FIG. 21 shows a side view viewed in the direction of the arrow [B] in FIG. 20. The reference sign [21C] in FIG. 21 shows a bottom view viewed in the direction of the arrow [C] in FIG. 20. FIG. 22 is a cross-sectional view taken along the line [22]-[22] in FIG. 21. FIG. 23 is a cross-sectional view conceptually showing a state where the image pickup unit of the present embodiment is held by the image pickup unit holding portion. Note that FIG. 23 is equivalent to the cross-sectional view in FIG. 22.

Basic configuration of the present embodiment is substantially the same as that of the above-described second embodiment. Therefore, in the description below, components which are the same as those in the first and second embodiments are attached with the same reference signs and detailed description thereof will be omitted, and only a part different from that of the first embodiment will be described in detail.

As shown in the drawings, an image pickup unit 20D of the present embodiment is different from that of the first and second embodiments in a form of a first electric substrate 21D of a solid electric substrate 23D. The second electric substrate 22B includes the flange 22Bf similarly as in the second embodiment.

The first electric substrate 21D includes an inclined region 21Dy formed with a predetermined inclination angle with respect to a substrate region 21Dx including an image pickup device mounting surface 21a (see FIG. 20).

In the substrate region 21Dx, the image pickup device mounting surface 21a and a bottom surface 21b are formed in parallel with each other. On the bottom surface 21b side of each of the substrate region 21Dx and the inclined region 21Dy, a part of the conductive circuit 26 is provided similarly as in the above-described respective embodiments. In addition, the cable connecting land 27 is formed in a tip region of the part of the conductive circuit 26. In this case, the cable connecting land 27 is provided on the bottom surface 21b side of the inclined region 21Dy. The signal transmission cable 28 is connected to the cable connecting land 27. The connecting part between the cable connecting land 27 and the signal transmission cable 28 is protected by the adhesive 29x or the like.

Furthermore, in the state where the image pickup unit 20D is incorporated in the distal end portion of the insertion portion of the endoscope, the inclined region 211Dy is arranged in a manner extending toward the proximal end side of the insertion portion of the endoscope. Other configurations are the same as those in the above-described second embodiment.

FIG. 23 shows the state where the image pickup unit 20D of the third embodiment thus configured is incorporated in the distal end portion of the insertion portion of the endoscope and held by the image pickup unit holding portion 30D. A configuration example in FIG. 23 shows a case where the image pickup unit 20D of the third embodiment is applied to an oblique-view endoscope, for example.

As shown in FIG. 23, the optical axis O of the image pickup optical system 25 housed in the second electric substrate 22B in the image pickup unit 20D is inclined with respect to an insertion axis Ax of the insertion portion of the endoscope. Such a configuration is enabled by the inclined region 21Dy being provided in the first electric substrate 21D. In other words, the image pickup unit 20D of the third embodiment is arranged such that, in the state where the image pickup unit 20D is incorporated in the distal end portion of the insertion portion of the endoscope, the plane of the inclined region 21Dy of the first electric substrate 21D is in parallel with the insertion axis Ax of the insertion portion.

In this case, the direction in which the arrow of the insertion axis Ax pointing as shown in FIG. 23 is defined as an insertion direction of the insertion portion. Then, as shown in FIG. 23, the image pickup unit 20D of the third embodiment is arranged such that, in the state where the image pickup unit 20D is incorporated in the distal end portion of the insertion portion of the endoscope, the inclined region 21Dy of the first electric substrate 21D extends toward the proximal end side of the insertion portion.

In this state, the position of the image pickup unit 20D is restricted by the position restricting surface 22Bfa of the flange 22Bf of the second electric substrate 22B contacting the flange contact surface 30a of the image pickup unit holding portion 30D. At this time, as shown in FIG. 23, in the first electric substrate 21D, the top surface side (on the same side as the image pickup device mounting surface 21a) of the inclined region 21Dy is adhered and fixed to the image pickup unit holding portion 30D with the adhesive 29x or the like.

Generally, after a signal transmission cable is connected to a cable connecting land of an electric substrate, an adhesive is applied to protect a connecting part between the signal transmission cable and the cable connecting land. When the adhesive hardens, thermal expansion occurs. At this time, if another component or the like is adhered on the adhesive, for example, there is a possibility that the position of the component changes and the optical axis O shifts, due to the thermal expansion of the adhesive.

In a configuration (not shown) in which the cable connecting land is provided on the top surface side of the first electric substrate 21D, for example, the amount of the adhesive to be applied after the signal transmission cable is connected to the cable connecting land becomes relatively large. The larger the application amount of the adhesive, the larger the thermal expansion. As a result, the position of the other component or the like adhered on the adhesive changes greatly, which causes a large shift of the optical axis O.

In view of the above, in the image pickup unit 20D of the present embodiment, the cable connecting land 27 is provided on the bottom surface 21b of the inclined region 21Dy of the first electric substrate 21D, to thereby provide a configuration in which the signal transmission cable 28 is connected to the bottom surface 21b side of the inclined region 21Dy of the first electric substrate 21D. With such a configuration, even in a case where the adhesive is applied to the image pickup device mounting surface 21a side of the first electric substrate 21D to ensure the adhering and fixing of the image pickup unit 20D to the image pickup unit holding portion 30D, the application amount of the adhesive can be reduced, to thereby be capable of suppressing the position shift of the optical axis O caused by the influence of the thermal expansion at the time when the adhesive hardens.

Furthermore, in the image pickup unit 20D, the image pickup device mounting surface 21a and the bottom surface 21b of the first electric substrate 21D are formed in parallel with each other, the bottom surface 21b opposing to the image pickup device mounting surface 21a. In addition, the image pickup device mounting surface 21a and the position restricting surface 22Bfa of the flange 22Bf are formed in parallel with each other. With such a configuration, the image pickup device mounting surface 21a, the bottom surface 21b opposing to the image pickup device mounting surface 21a, and the position restricting surface 22Bfa of the flange 22Bf are in parallel with one another.

From the above, when the image pickup unit 20D is pressed from the bottom surface 21b side of the first electric substrate 21D toward the direction along the optical axis O (see the direction of the arrow Z1 in FIG. 23), the position restricting surface 22Bfa of the flange 22Bf contacts the flange contact surface 30a of the image pickup unit holding portion 30D. Such a configuration enables the image pickup unit 20D to be pressed in a sure and stable state. As a result, position adjustment of the image pickup unit 20D can be performed while suppressing the position shift of the optical axis O of the image pickup unit 20D.

Figure 24:
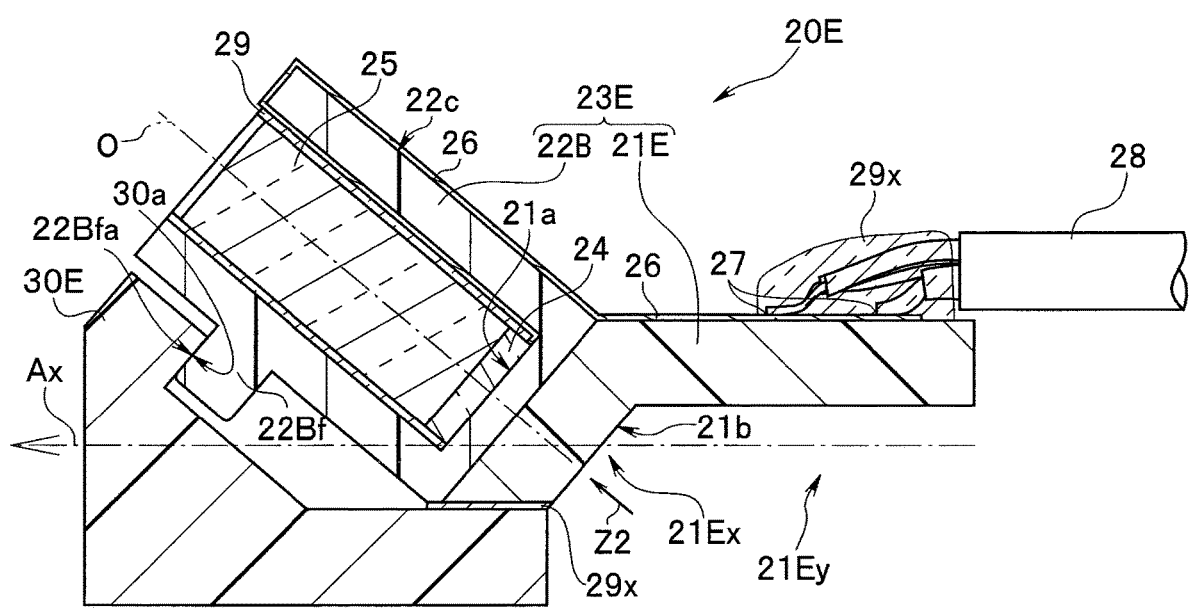
FIG. 24 is a cross-sectional view showing a modification of the image pickup unit of the third embodiment of the present invention.

The configuration in the third embodiment can be modified as described below. FIG. 24 is a view showing a modification of the image pickup unit of the third embodiment of the present invention. FIG. 24 is a cross-sectional view conceptually showing the state where the image pickup unit of the present modification is held by the image pickup unit holding portion.

An image pickup unit 20E of the present modification is applied to an oblique-view endoscope similarly as the image pickup unit 20D of the above-described third embodiment. The image pickup unit 20E of the present modification is different from the image pickup unit 20D of the third embodiment in an inclined manner of the optical axis O of the image pickup optical system 25 with respect to the insertion axis Ax. In the third embodiment, the optical axis O inclines toward the proximal end side in the direction along the insertion axis Ax. In contrast, in the present modification, the optical axis O inclines toward the insertion direction side in the direction along the insertion axis Ax.

In the image pickup unit 20E of the present modification includes an inclined region 21Ey formed with a predetermined inclination angle with respect to a substrate region 21Ex including an image pickup device mounting surface 21a of a first electric substrate 21E. The image pickup device mounting surface 21a and a bottom surface 21b of the substrate region 21Ex are formed in parallel with each other. In addition, in the state where the image pickup unit 20E is incorporated in the distal end portion of the insertion portion of the endoscope, the inclined region 21Ey is arranged to extend toward the proximal end side of the insertion portion of the endoscope. In such points, the image pickup unit 20E is basically the same as the image pickup unit of the third embodiment.

In addition, in the first electric substrate 21E, a part of the conductive circuit 26 is provided on the image pickup device mounting surface 21a side of the inclined region 21Ey. The cable connecting land 27 is formed in a tip region of the part of the conductive circuit 26. The signal transmission cable 28 is connected to the cable connecting land 27. The connecting part between the cable connecting land 27 and the signal transmission cable 28 is protected by the adhesive 29x or the like. In addition, the distal end of the part of the conductive circuit 26 is connected to a part of the conductive circuit 26 on the first surface 22c of the second electric substrate 22B.

On the other hand, the second electric substrate 22B includes the flange 22Bf, and formed in substantially the same manner as in the second and third embodiments. Other configurations are the same as those in the third embodiment.

FIG. 24 shows the state where the image pickup unit 20E of the third embodiment thus configured is incorporated in the distal end portion of the insertion portion of the endoscope and held by an image pickup unit holding portion 30E.

As shown in FIG. 24, the optical axis O of the image pickup optical system 25 housed in the second electric substrate 22B in the image pickup unit 20E is arranged so as to be inclined with respect to the insertion axis Ax of the insertion portion of the endoscope.

In this state, the position of the image pickup unit 20E is restricted by the position restricting surface 22Bfa of the flange 22Bf of the second electric substrate 22B contacting the flange contact surface 30a of the image pickup unit holding portion 30E.

At this time, as shown in FIG. 24, a part of the first electric substrate 21E is eventually adhered and fixed to a part of the image pickup unit holding portion 30E with the adhesive 29x or the like. As a result, the image pickup unit 20E is held stably with respect to the image pickup unit holding portion 30E.

In addition, as described above, in the image pickup unit 20E, the image pickup device mounting surface 21a and the bottom surface 21b of the first electric substrate 21E are formed in parallel with each other, the bottom surface 21b opposing to the image pickup device mounting surface 21a. In addition, the image pickup device mounting surface 21a and the position restricting surface 22Bfa of the flange 22Bf are formed in parallel with each other.

From the above, when the image pickup unit 20E is pressed from the bottom surface 21b side of the first electric substrate 21E in the direction (see the direction of the arrow Z2 in FIG. 24) along the optical axis O, the position restricting surface 22Bfa of the flange 22Bf contacts the flange contact surface 30a of the image pickup unit holding portion 30E. Such a configuration enables the image pickup unit 20E to be pressed in a sure and stable state. As a result, position adjustment of the image pickup unit 20E can be performed while suppressing the position shift of the optical axis O of the image pickup unit 20E.

Note that the following known technique is used, for example, to form the conductive circuit on the surface of the solid electric substrate in the image pickup unit of each of the embodiments.

The solid electric substrate is formed by the MID using a resin containing a metal catalyst, for example. Then, a desired pattern portion on the surface of the MID is irradiated with laser, to activate the metal catalyst. After that, non-electrolytic plating is applied, and thereby the pattern of the conductive circuit is formed.

Such an irradiation with laser in the manufacturing process is performed on the surface of the solid electric substrate, for example. At this time, the surface of the irradiation target has to be sufficiently exposed outside. For example, in the case where the surface of the solid electric substrate is formed with inclination, if the inclination angle is an acute angle, there is a case where the surface of the substrate cannot be irradiated sufficiently with laser. If the irradiation with laser is not sufficient, the metal catalyst cannot be activated sufficiently. Therefore, there is a possibility that the wiring pattern (conductive circuit) to be formed is not surely precipitated. If such precipitation insufficiency of the wiring pattern occurs, signal transmission would not be able to be surely performed, which might cause degradation of transmission quality. For example, if degradation of transmission occurs in the conductive circuit that transmits image signals, an image quality of a display image might be degraded.

In order to form the wiring pattern (conductive circuit) surely with high accuracy, in the solid electric substrate, the part at which the conductive circuit is provided is formed in such a shape that the part can be surely irradiated with laser.

The present invention is not limited to the above-described embodiments, and it goes without saying that various modifications and applications can be implemented within a range without departing from the subject matter of the invention. Furthermore, the above embodiments include inventions at various stages, and various inventions can be extracted by appropriate combinations of plural disclosed constituent elements. For example, even if some of the constituent elements are removed from all the constituent elements shown in the respective embodiments, a configuration from which the constituent elements are eliminated can be extracted as an invention insofar as the configuration can solve the problem to be solved by the invention and attain the effects of the invention. Furthermore, constituent elements over different embodiments may be appropriately combined.

The invention is not limited by the specific embodiments except as limited by appended claims.

What is claimed is:

1. An image pickup unit comprising:
   an image pickup optical system including an optical axis;
   an image pickup device configured to pick up an optical image formed by the image pickup optical system;
   a first electric substrate on which the image pickup device is mounted;
   a second electric substrate configured of a component formed integrally with the first electric substrate, the second electric substrate being configured to surround peripheries of the image pickup optical system and the image pickup device and extend in a direction along the optical axis, the second electric substrate including a housing space for housing the image pickup optical system and the image pickup device, an inside of the housing space having a quadrangular prism shape, at least a part of the second electric substrate being formed in an arc shape when viewed in a cross section in a vertical direction with respect to the optical axis; and
   a conductive circuit configured to connect the first electric substrate and the second electric substrate, the conductive circuit being provided continuously from a first surface to a second surface of the second electric substrate, the first surface being exposed outside, the second surface facing the periphery of the image pickup optical system in the housing space.

2. The image pickup unit according to claim 1, wherein at least a part of an outer circumference of the second electric substrate further has an arc shape when viewed in the cross section in the vertical direction with respect to the optical axis.

3. The image pickup unit according to claim 2, wherein the outer circumference of the second electric substrate has a cylindrical shape extending in the direction along the optical axis.

4. The image pickup unit according to claim 1, wherein in the first electric substrate, a surface on which the image pickup device is mounted and another surface opposing to the surface on which the image pickup device is mounted are in parallel with each other.

5. The image pickup unit according to claim 4, wherein
a light-receiving surface of the image pickup device mounted on the first electric substrate is placed vertically to the optical axis of the image pickup optical system.

6. The image pickup unit according to claim 1, wherein
the first electric substrate includes a cable connecting land configured to connect a signal transmission cable and the conductive circuit, the signal transmission cable being configured to transmit and receive an electric signal between an external apparatus and the image pickup device, and
the conductive circuit is connected to the cable connecting land via the first surface and the second surface of the second electric substrate.

7. The image pickup unit according to claim 6, wherein
the first electric substrate includes a surface on which the image pickup device is mounted and another surface on which the cable connecting land is disposed.

8. The image pickup unit according to claim 1, wherein
the second electric substrate extends from a part at which the image pickup device and the first electric substrate are connected to each other in a direction along the optical axis, to cover side surfaces of the image pickup optical system.

9. The image pickup unit according to claim 1, wherein
the second electric substrate includes a flange configured to determine a position of the image pickup unit with respect to an image pickup unit holding portion.

10. The image pickup unit according to claim 9, wherein
the flange in the second electric substrate includes a cutout part formed by a part of the flange being cut in a circumferential direction, and
the conductive circuit is formed to pass through the cutout part.

11. The image pickup unit according to claim 1, wherein
at least a part of the first electric substrate is formed in an arc shape when viewed in the cross section in the vertical direction with respect to the optical axis.

12. An endoscope comprising:
an image pickup unit comprising:
an image pickup optical system including an optical axis;
an image pickup device configured to pick up an optical image formed by the image pickup optical system;
a first electric substrate on which the image pickup device is mounted;
a second electric substrate configured of a component formed integrally with the first electric substrate, the second electric substrate being configured to surround peripheries of the image pickup optical system and the image pickup device and extend in a direction along the optical axis, the second electric substrate including a housing space for housing the image pickup optical system and the image pickup device, an inside of the housing space having a quadrangular prism shape, at least a part of the second electric substrate being formed in an arc shape when viewed in a cross section in a vertical direction with respect to the optical axis; and
a conductive circuit configured to connect the first electric substrate and the second electric substrate, the conductive circuit being provided continuously from a first surface to a second surface of the second electric substrate, the first surface being exposed outside, the second surface facing the periphery of the image pickup optical system in the housing space;
an insertion portion configured to be inserted into a subject in a predetermined insertion direction; and
an image pickup unit holding portion provided at a distal end of the insertion portion, and configured to hold the image pickup unit.

13. The endoscope according to claim 12, wherein
at least a part of an outer circumference of the second electric substrate further has an arc shape when viewed in the cross section in the vertical direction with respect to the optical axis.

14. The endoscope according to claim 13, wherein
the outer circumference of the second electric substrate has a cylindrical shape extending in the direction along the optical axis.

15. The endoscope according to claim 12, wherein
in the first electric substrate, a surface on which the image pickup device is mounted and another surface opposing to the surface on which the image pickup device is mounted are in parallel with each other, and
a light-receiving surface of the image pickup device mounted on the first electric substrate is placed vertically to the optical axis of the image pickup optical system.

16. The endoscope according to claim 12, wherein
the image pickup unit holding portion is provided at a position at which the image pickup unit holding portion holds the image pickup unit with the optical axis inclined with respect to the insertion direction, and applied to an oblique-view endoscope.

17. The endoscope according to claim 16, wherein
the first electric substrate includes a surface on which the image pickup device is mounted and a surface on which a cable connecting land is disposed, the cable connecting land being configured to connect a signal transmission cable and the conductive circuit, the signal transmission cable being configured to transmit and receive an electric signal between an external apparatus and the image pickup device, and
the cable connecting land is provided on a proximal end side in the insertion direction in which the insertion portion is inserted into the subject.

18. The endoscope according to claim 17, wherein
the first electric substrate is formed such that the surface on which the image pickup unit is mounted is formed to be inclined with respect to the surface on which the cable connecting land is disposed, and
the surface on which the image pickup unit is mounted and a surface opposing to the surface on which the image pickup unit is mounted are in parallel with each other, the surface opposing to the surface on which the image pickup unit is mounted being located on a side where the signal transmission cable is connected to the cable connecting land.

19. The endoscope according to claim 12, wherein
the second electric substrate includes a flange configured to determine a position of the image pickup unit in a rotation direction around the optical axis, with respect to the image pickup unit holding portion.

20. The endoscope according to claim 19, wherein
the second electric substrate includes a contact surface configured to contact a part of the image pickup unit holding portion to determine a position of the image pickup unit in the direction along the optical axis, and the flange in the second electric substrate includes a cutout part formed by a part of the flange being cut in a circumferential direction, and the conductive circuit is formed to pass through the cutout part.

* * * * *